US006562957B1

(12) United States Patent
Letarte et al.

(10) Patent No.: US 6,562,957 B1
(45) Date of Patent: May 13, 2003

(54) GENOMIC SEQUENCE ENCODING ENDOGLIN AND FRAGMENTS THEREOF

(75) Inventors: Michelle Letarte, Toronto (CA); Douglas A. Marchuk, Chapel Hill, NC (US); Kimberly McAllister, Durham, NC (US)

(73) Assignees: HSC Research & Development Limited Partnership (CA); Duke University, Durham, NC (US)

( * ) Notice: Subject to any disclaimer, the term of this patent is extended or adjusted under 35 U.S.C. 154(b) by 0 days.

(21) Appl. No.: 09/506,859

(22) Filed: Sep. 28, 1999

Related U.S. Application Data

(63) Continuation of application No. 08/346,129, filed on Apr. 29, 1994, now abandoned.

(51) Int. Cl.$^7$ .................. C07H 21/04; C07H 19/00; C12N 1/20; C07K 17/00; C12P 16/00
(52) U.S. Cl. .................. 536/23.5; 536/22.1; 536/23.1; 536/23.5; 536/24.33; 435/252.3; 530/350; 530/388.2
(58) Field of Search ................ 536/22.1, 23.1, 536/23.5, 24.33; 435/252.3; 530/350, 388.2

(56) References Cited

PUBLICATIONS

Johnson, "Endoglin, TGF–beta binding protein of endothelial cells . . . ", Nat. Genet. vol. 8, No. 4, pp. 345–351 (1994).*
Bellón, T., et al., "Identification and Expression of Two Forms of the Human Transforming Growth Factor–β–binding Protein Endoglin with Distinct Cytoplasmic Regions", 1993, Eur. J. Immunol., 23:2340–45.
Braverman, I., et al., "Ultrastructure and Three–Dimensional Organization of the Telangiectases of Hereditary Hemorrhagic Telangiectasia", 1990, J. Investigative Dermatology, 95:422–27.
Cheifetz, S., et al., Endoglin Is a Component of the Transforming Growth Factor–β Receptor System in Human Endothelial Cells, 1992, J. Biological Chem., 267:19027–30.
Dumont, D., et al., "Dominant–negative and Targeted Null Mutations in the Endothelial Receptor Tyrosine Kinase, tek, Reveal a Critical Role in Vasculogenesis of the Embryo", 1994, Genes & Develop., 8:1897–909.
Fernández–Ruiz E., et al., "Assignment of the Human Endoglin Gene (END) to 9q34→qter", 1993, Cytogenet. Cell Genet., 64:204–207.
Franzén, P., et al., "Cloning of a TGFB Type I Receptor That Forms a Heteromic Complex with the TGFβ Type II Receptor", 1993, Cell, 75:681–92.
Gougos, A., et al., "Primary Structure of Endoglin, and RGD–containing Glycoprotein of Human Endothelial Cells", 1990, J. Biol. Chem., 265:8361–64.

Gougos, A., et al., "Identification of Distinct Epitopes of Endoglin, and RGD–containing Glycoprotein of Endothelial Cells, Leukemic Cells, and Syncytiotrophoblasts", 1992, Int'l Immunology, 4:83–92.
Hashimoto, K., et al., "Hereditary Hemorrhagic Telangiectasia", 1972, Oral Surg., 34:751–67.
Jahnke, V., "Ultrastructure of Hereditary Telangiectasia", 1970, Arch. Otolaryng., 91:262–65.
Jennings, J., et al., "Comparison of the Biological Actions of TGF Beta–1 and TGF Beta–2: Differential Activity in Endothelial Cells", 1988, J. Cellular Physiol., 137:167–72.
Lastres, P., et al., "Regulated Expression on Human Macrophages of Endoglin, an Arg–Gly–Asp–containing Surface Antigen", 1992, Eur. J. Immunol., 22:393–97.
López–Casillas, F., et al, "Structure and Expression of the Membrane Proteoglycan Betaglycan, a Component of the TGF–β Receptor System", 1991, Cell, 67:785–95.
López–Casillas, F., et al, Betaglycan Presents Ligand to the TGFβ Signaling Receptor, 1993, Cell, 73: 1435–44.
Luscinskas, F., et al., "Integrins as Dynamic Regulators of Vascular Function", 1994, FASEB J., 8:929–38.
Madri, J., et al., "Interactions of Vascular Cells with Transforming Growth Factors–β$^α$", 1990, Annals of NY Acad Sciences, 593:243–58.
Menefee, M., et al., "Hereditary Hemorrhagic Telangiectasia (Osler–Weber–Rendu Disease)", 1975, Arch. Otolaryngol., 101:246–51.
Mathew, S., et al., "Transforming Growth Factor Receptor Gene TGFBR2 Maps to Human Chromosome Band 3p22", 1994, Genomics, 20:114–15.
Millauer, B., et al., "High Affinity VEGF Binding and Developmental Expression Suggest Flk–1 as a Major Regulator of Vasculogenesis and Angiogenesis", 1993, Cell, 72:835–46.
Morén, A., et al., "Molecular Cloning and Characterization of the Human and Porcine Transforming Growth Factor–β Type III Receptors", 1992, Biochem. and Biophys. Res. Commun., 189:356–62.
Schnürch, H., et al., "Expression of tie–2, a Member of a Novel Family of Receptor Tyrosine Kinases, in the Endothelial Cell Lineage", 1993, Development, 119:957–68.
Shovlin, C., et al., "A Gene for Hereditary Haemorrhagic Telangiectasia Maps to Chromosome 9q3", 1994, Nature Genetics, 6:205–209.

(List continued on next page.)

Primary Examiner—Gary Benzion
Assistant Examiner—Joyce Tung
(74) Attorney, Agent, or Firm—Fish & Richardson P.C.

(57) ABSTRACT

A method of diagnosing hereditary haemorrhagic telangiectasia (HHT) which includes the steps of:
  obtaining a sample of genomic DNA from a patient or fetus; and
  determining whether the DNA contains a mutation in a gene encoding endoglin, betaglycan, TGF-β type I receptor (RI), TGF-β type II receptor (RII), or TGF-β/ activin type I receptor (TSR-I), such a mutation being an indication that the patient or fetus bears a gene making the patient or fetus susceptible to HHT.

3 Claims, 14 Drawing Sheets

PUBLICATIONS

St.–Jacques, S., et al., "Molecular Characterization and in Situ Localization of Murine Endoglin Reveal that is a Transforming Growth Factor–β Binding Protein of Endothelial and Stromal Cells", 1994, *Endocrinology*, 134:2645–57.

Wang, X., et al., "Expression Cloning and Characterization of the TGF–β Type III Receptor", 1991, *Cell*, 67: 797–805.

White, M., et al., "Detecting Single Base Substitutions as Heteroduplex Polymorphisms", 1992, *Genomics*, 12: 301–306.

Wrana, J., et al., "TGFβ Signals Through a Heteromeric Protein Kinase Receptor Complex", 1992, *Cell*, 71: 1003–14.

Wrana, J., et al., "Mechanism of Activation of the TGF–β Receptor", 1994, *Nature*, 370:341–47.

Attisano et al., "Identification of human Activin and TGFb Type I Receptors that Form Heteromeric Kinase Complexes with Type II Receptors", 1993, *Cell* 75:671–680.

Heutink et al., "Linkage of hereditary haemorrhagic telangiectasia to chromosome 9q34 and evidence for locus heterogeneity", 1994, *J. Med. Genet.*, 31:933–936.

Lin et al., "Expression Cloning of the TGF–b type II receptor, a functional transmembrane serine/threonine kinase", 1992, *Cell* 68:775–785.

McAllister et al., "Genetic heterogeneity in hereditary heamorrhagic telangiectasia: possible correlation with clinical phenotype", 1994, *J. Med. Genet.*, 31:927–932.

McDonald et al., "A disease locus for hereditary haemorrhagic telangiectasia maps to chromosome 9q33–34", 1994, *Nature Genetics*, 6:197–204.

Porteous et al., "Genetic heterogeneity in hereditary haemorrhagic telangiectasia", 1994, *J. Med. Genet.*, 31:925–926.

Yamashita et al., "Endoglin forms of Heteromeric Complex with the signaling receptors for transforming growth factor–b", 1994, *J. Biol. Chem.*, 269:1995–2001.

Ge et al., "Cloning and expression of a cDNA encoding mouse endoglin, an endothelial cell TGF–b ligand" 1994, *Gene*, 138:201–206.

McAllister et al., "Endoglin, a TGF–b binding protein of endothelia cells, is the gene for hereditary haemorrhagic telangiectasia type 1", 1994, *Nature Genetics*, 8:345–351.

O'Connell et al., "Endoglin: a 180–kD endothelial cell and macrophage restricted differentiation molecule", 1992, *Clin. Exp. Immunol.*, 90:154–159.

* cited by examiner

Exon 1

1    ATGGACCGCGGCACGCTCCCTCTGGCTGTTGCCCTGCTGTGCTGGCTGCAGCCTCAGCCCCACAAGTCTCTGCAGAAACAGTCCATTGT
1    MetAspArgGlyThrLeuProLeuAlaValAlaLeuLeuLeuAlaSerCysSerLeuSerProThrSerLeuAlaGluThrValHisCys

Exon 2

91   GACCTTCAGCCTGTGGGCCCCCGAGAGGGCGAGGTGACATATACCACTAGCCAGGTCTCAGAAGGGCTGCTGCTCAGGCCCCCAATGCC
31   AspLeuGlnProValGlyProGluArgGlyGluValThrTyrThrThrSerGlnValSerLysGlyCysValAlaAlaProAsnAla

181  ATCCTTGAAGTGCCATGTCCTCTTCCTGAGTTCCAACGGGCCCGTCACAGCTGGACTGGAGCTGACTCTCCAGGCATCCAAGCAAAATGGCACC
61   IleLeuGluValHisValLeuPheLeuGluProSerGlnLeuGluLeuThrLeuGlnLeuAlaSerLysGlnAsnGlyThr

Exon 3

271  TGGCCCCGAGAGGTGCTTCTGGTCCTCAGTGTAAACAGCAGTGTCTTCCTGCATCCCAGGCCCTGGAATCCCACTGCACTTGGCCTAC
91   TrpProArgGluValLeuLeuValLeuSerValAsnSerSerValPheLeuHisProArgProLeuAsnProThrAlaTyr

Exon 4

361  AATTCCAGCCTGGTCACCTTCCAAGAGCCCCGGGGTCAACACCACAGAGCTGCCATCCTTCCCAAGACCTGGACCCAGATCCTTGAGTGGGCA
121  AsnSerSerLeuValThrPheGlnGluProProGlyValAsnThrThrGluLeuProLysThrGlnIleLeuGluTrpAla

Exon 5

451  GCTGAGAGGGCCCATCACCTCTGCTGAGCTGAATGACCCCAGAGCATCCTCCGACTGGGCCAAGCCAGGGCTCACTGTCC
151  AlaGluArgGlyProIleThrSerAlaAlaGluLeuAsnAspProGlnSerIleLeuLeuArgLeuArgLeuGlyAlaGlnAlaGlyLeuThrValSer

541  TTCTGCATGCTGGAAGCCAGCCAGGACATGGGCGCCGTCGAGTGGGCCCGCCTACTCCAGCCTTGGTCCGGGGCTGCCACTTGGAA
181  PheCysMetLeuGluAlaSerGlnAspMetGlyArgThrLeuGluTrpArgProArgProAlaLeuValArgGlyCysHisLeuGlu

FIG. 1A

```
631   GGCGTGGCCGGCCACAAGGAGGCGCACATCCTGAGGGTCCTGCCGGGCCACTCGGCCGGGCCCCGGACGGTGAAGGTGAACTG
211   GlyValAlaGlyHisLysGluAlaHisIleLeuArgValLeuProGlyHisSerAlaGlyProArgThrValLysValGluLeu
                                  Exon 6
722   AGCTGCGCACCCGGGATCTCGATGCCGTCCTTCATCCTGCAGGTCCCCCCTACGTGTCCTGGCTCATCGACGCCAACCACATGCAG
241   SerCysAlaProGlyAspLeuAspLeuAspAlaValLeuIleLeuGlnGlyProProTyrValSerTrpLeuIleAspAlaAsnHisAsnMetGln 811   ATCTGGACCACTGGAGAATACTCCTTCAAGATCTTTCCAGAGAAAAACATTCGTGGCTTCAAGCTCCCAGACACACCTCAAGGCCTCCTG
271   IleTrpThrThrGlyGluTyrSerPheLysIlePheProGluLysAsnIleArgGlyPheLysLeuProAspThrProGlnGlyLeuLeu
                                                            Exon 7
901   GGGGAGGCCCGAGTGCTCAATGCCAGCATCCTTCGTGGAGCTACCGCTGGCCAGCATTGTCTCACTTCATGCCTCCAGCTGC
301   GlyGluAlaArgMetLeuAsnAlaSerIleValAlaSerPheValGluLeuProLeuAlaSerIleValSerLeuHisAlaSerCys
                                   Exon 8
991   GGTGGTAGGCTGCAGACCCTCACCCGACCGATCCAGACCCCCAAGGACACTTGTAGCCCGGAGCTGCTCATGTCCTTGATCCAG
331   GlyGlyArgLeuGlnThrSerProAlaProIleGlnThrThrProProLysAspThrCysSerProGluLeuLeuMetSerLeuIleGln 1081  ACAAAGTGTGCCGACGACGCCATGACCCTGGTACTAAAGAAAAGAGCTTGTTGCCATTGAAGTGCACCATCACGGGCCTGACCTTCTGG
361   ThrLysCysAlaAspAspAlaMetThrLeuValLeuLysLysGluLeuValAlaHisLeuLysCysThrIleThrGlyLeuThrPheTrp
                                       Exon 9
1171  GACCCCAGCTGTGAGGCAGAGGACAGGGGTGACAAGTTTGTCTTGCCAGTGCTTACTCCAGTCTGTGGCATGCAGGTGTCAGCAAGTATG
391   AspProSerCysGluAlaGluAspArgGlyAspLysPheValLeuArgSerAlaTyrSerSerCysGlyMetGlnValSerAlaSerMet 1261  ATCAGCAATGAGGCCGTTGGTTGTTGCAATATCCTGTGCAGCTTCATCATCGAGCTCTCAATCCAGCGGAAAAAGGTGCACTGCCTCAACATGACCAGCCCTCTCTTTTC
421   IleSerAsnGluAlaValValAlaAsnIleLeuSerSerSerProGlnArgLysLysValHisCysLeuAsnMetThrSerLeuSerPhe
```

FIG. 1B

Exon 10

1351  CAGCTGGGCCTCTACTCAGCCTCCAACACTTCCTCCAGGCCTCCAACACCATCGAGCCGGGCAGCAGAGCTTTGTGCAGGTCAGAGTGTCC
451   GlnLeuGlyLeuTyrLeuSerProHisPheLeuLeuGlnAlaSerAsnThrIleGluProGlyGlnGlnSerPheValGlnValArgValSer

1441  CCATCCGTCTCCGAGTTCCTGCTCCAGTTAGACAGCTTGGGCCTGGACTTGGGAGGAGGCCTGAGGAGGAACTCATCCAGGGCCGG
481   ProSerValSerGluPheLeuLeuGlnLeuAspSerCysHisLeuLeuAspLeuGlyGlyThrValGluLeuIleGlnGlyLysArg

Exon 11

1531  GCGGCCAAGGGCAACTGTGTGAGCCTGCTGTCCCCAAGCCCCGAGGTGACCCCGCGCTTCAGCTTCCTCCACTTCTACACAGTACCC
511   AlaAlaLysGlyAsnCysValSerLeuLeuSerProSerProGluGlyAspProArgPheSerPheLeuHisPheTyrThrValPro

1621  ATACCCAAAAACCGGACACCCTCAGTGCACGGTAGCCCTGCGTCCAAGACCGGGTCTCAAGAAGTCCATAGGACTGTCTTCATG
541   IleProLysThrGlyThrLeuSerCysThrValAlaLeuArgProLysThrGlySerGlnGluValHisArgThrValPheMet

Exon 12 Exon 13

1711  CGCTTGAACATCATCAGCCCTGACCTGTCTGGTTGCACAAGGCAAAGGCTCCTCGTCTGCCCGCGTTGCATCACCTTTGGTGCCTTC
571   ArgLeuAsnIleIleSerProAspLeuSerGlyCysThrArgGlnGlySerLeuValLeuProAlaValLeuIleThrPheGlyAlaPhe

1801  CTCATCGGGGCCCTGCTCACTGCTGCACTCTGGTACATCTACTGGTACATCTACTGGACAACGCGTTCCCCAGCAAGCGGGAGCCCGTGGTGGCGGTGCT
601   LeuIleGlyAlaLeuLeuThrAlaLeuLeuThrTyrSerHisThrArgSerProSerLysArgGluProValValAlaValAla

Exon 14

1891  GCCCCGGCCTCCTCGGAGAGCAGCAGCAGCCAACCACAGCATGGGAGCACTCAGAGACACCCCTGCTCCACCAGCAGCATGGCATAGCCC
631   AlaProAlaSerSerSerGluSerSerSerThrAsnHisSerIleGlySerThrProCysSerSerMetAla***

CGGACCCCCGCCTCGCCGCTGCGCGCAGGAGGAGCAGCCGGCGAGCAGCCCAGCTGGGACACTGGTGTGAACTCACCTGGAGCACTTCCTCCACT
      CGACCCAGAATGGAGCCCTCTCGCCTGCCCTCCCGCCCTCCCCCTCCCCTCCAGAGCCCCTCTCAGAGGCCTCAGCCACTGCAGCCTGCTTGAACACC
      TTGGGGTCCCTCCACCCAGCAACCTTCAACCCAGTGGGTCTGGAGATATGGCTGCCCAGGAGCAGAGACAGACCACTTGCCACGCTGTTGTAAA
      AACCCAAGTCCCTGTCATTGAACCTGGATC

FIG. 1C

```
         820
          |
Normal    ACT GGA GAA TAC TCC TTC AAG
          Thr Gly Glu Tyr Ser Phe Lys Mutant    ACT GGA GAA TAG TCC TTC AAG
          Thr Gly Glu ***
```

FIG. 2C

```
         874
          |
Normal    CTC CCA GAC ACA CCT CAA GGC CTC CTG GGG GAG GCC CGG ATG CTC AAT GCC AGC ATT
          Leu Pro Asp Thr Pro Gln Gly Leu Leu Gly Glu Ala Arg Met Leu Asn Ala Ser Ile Mutant                                                                  CTC CCA GAT GCC AGC ATT
                                                                        Leu Pro Asp Ala Ser Ile
```

FIG. 3A

```
         1543
          |
Normal    AAC TGT GTG AGC CTG CTG TCC CCA AGC CCC GAG GGT GAC
          Asn Cys Val Ser Leu Leu Ser Pro Ser Pro Glu Gly Asp Mutant    AAC TGT GTG ACT GCT GTC CCC AAG CCC CGA GGG TGA
          Asn Cys Val Thr Ala Val Pro Lys Pro Arg Gly ***
```

FIG. 4C

Exon 1

ATGGACCGCGGCACGCTCCCCTCTGGCTGTTGCCCTGTGCTGTGGCCAGCTGCAGCCCCACAA-----aatccatgaacgaataatgatat p27 for
cacctcataaggtggctgtgatgatgcaggaagcngttagctcatgtcaagtccctaggagacgtttggaaagtaggagtcattgtcatcaccttat Exon 2 tctcacctgccctcttccggatgtttctccaacagGTCTTGCAGAAACAGTCCATTGTGACCTTCAGCCTGTGGGCCCTGTGGGGCGAGGTGACA TATACCACTAGCCAGGTCTCGAAGGGCTGGTGCTCAGGCCCCCAATGCCATCCTTGAAGTCCAATGTCCCTCTTCCTGGAGTTCCAACGtgagtgt p27 rev
cccatggcagggtcgggtgggggctcagaggaagctccaaggcagatgggtgaggggtgccttccttggctgtgtccctgggcagtggctgagtcc tcgttagcccctgccaagagagtgatgtgggcatctcacagggccataagaggtggcatttcta-----GGCCCGTCACAGCTGGAGCTGACTCTC Exon 3
CAGGGCATCCAAGCAAAATGGCACCTGGCCCCGAGAGTGCTTCTGGTCCTCAGTGTAAACAGCAGTGTCTTCCTGCATCTCCAGGCCCTGGGAATCCC p322 for
ACTGCACTTGGCCTAC-----ggcctctcttctctcagccatatggctgactccacaaattacttcctgacctcctacatggatagagagggcacagg Exon 4 gcaggaacagcgtgctgagcctgagcctccacatgtctcccccagAATTCCAGCCTGTCACCTTCCAAGAGCCCCGGGGGTCAACACCACAGAGCTGCCATCC

FIG. 5A

```
TTCCCCAAGACCCAGATCCTTGAGTGGGCAGCTGAGAGGGCCCATCACCTCTGCTGCTGAGCTGAATGACCCCAGAGCATCCTCCTCCGACTGGG
                                                                              p322 rev
ccaAGgtcagttcccagcaacctctggcctcatgatactgctcaggaggaatctgagctgctcctgcccacacctcaaacttgggcaccaagg
gtgcaggaggggacacgctgtgccacagttcacatgccacaagcagtgctgcctggacagtgatggctcctccaccaaatatcagattgaagcat
gtggaatatgccaggttctgacctaaa------ttggcaggtagtggtggaaggaagttcgaacctaggtcctctgagcctctccctctgcagcasc
                      p486 for
gtcctgcctgccccaccactatctttggctgtgggtgagggcgggctctgttagggcaggggctgctga----CCCAGGGGTCACTGTCCTTCTGCA
         Exon 5
TGCTGGAAGCCAGCAGGACATGGGCCGCTCGAGTGCCCGGTACTCCAGCCTTGGTCCGGGCTGCCACTGGAAGGCGTGGCCGGCCAC
AAGGAGGCGCACATCCTGAGGGTCCTGCCCGGGGCCACTCGGGCGGGtatggctctcgccccgccctgacactagtcccaccccgagaccaccccc
                                               p486 rev
ctgacccccccgccccctctccgtccctatasagcccaccccagtcccagaccccgcgcagccctgtgagagcacagtcgctttctc
ctactctaggctacgcccccatggcccctttccctttgggcacaagctgcccagtcccatcccataaaccacacctgccaggtaag
                                                      p650 for
agtgcagccgccgccaccgacgcaggcctcgctcccgcctgctcccttcagtgttcatcgcgtctgtctcccgcaggCGCCGGACG
                                            Exon 6
GTGACGGTGAAGGTGGAACTGAGCTGCGACCTGGGGATCTCGATGCCGTCCTCATCCTGCAGGGTCCCCCTACGTGTCCTGGCTCATCGACGCCAA
                                                      p650 rev
CCCAAACATGCAGATCGGgtgagttgtgcgcagctcccgggacacaaaccaaactcccaacctctggatcagggaagtttctgtgaaggtgaac
```

FIG. 5B cccgagttgagctgaaggacaaatcacctatgcccatacgtgaggaagggggcaggcagaagacgcagcaggagtgggggacacagcaggaccgagg p778 for
cctggcataacccctggctggctggcacagactgtgtccatgccccctgttctgcctctctcccacattagACCACTGGAGAATACTCCT Exon 7
TCAAGATCTTTCCAGAGAAAACATTCGTGGCTTCAAGCTCCCAGACACACCTCAAGGCCTCCTGGGGAGGCCCGGATGCTCAATGCCAGCATTGTG GCATCCTTCGTGGAGCTACCGCTGCCAGCATTGTCTCACTTCATGCCTCCAGCTGCGgtgagcacccttcccctgccctcccttccctcccctcg p778 rev
cttggatcagtggccacactgttggtgaagcacctctgtgtgagcttgggcaagtacatcagcctctctgagcctcattttctcatctgcacatgg gaacaatgggagtagctaatcatagaagagcctgagaatcgcttgaacctgggagttgcagtgagcaagatcgtgccactgcactcccag pX8 for
cccgggtaacagagcaaaactccgtctcaaaaaaaaaaaagcctggtgcggcacacatatcacacagtaccagccgcctggcctg Exon 8
cctct-c-acccacagGTGGTAGGCTGCAGACCTCACCCGCACCGATCCAGACCACTCCTCCAAGGACACTTGTAGCCCCGGAGCTGCTCATGTCCT TGATCCAGACAAAGTGTCCGACGACGCCATGACCCTGGTACTAAAGAAAGAGCTTGTTCGGtaagggaactcctgccctctggctcaggatgaca pX8 rev
tggacatctgattcctccctagccaagaccctttgggggtcctagcccaggcccaggcaggggggcaagtcacgtccctctgcaagccttagttttcccacttgt

FIG. 5C

```
ataatggaattgataatggtacctaccacgtggtgagaattaaaggcagtctgacaggccaatcacgtggcacagtaagatgtggtacatagtaagtg cttagtaaataatgcagcactagtagtt------gCATTGAAGTGCACCATCACGGGCCTGACCTTCTGGACCCCAGCTGTGAGGCAGAGGACAGG
                                   Exon 9
GGTGACAAGTTTGTCTTGCGCAGTGCTTACTCCAGTGTGGCAGGTGTCAGCAAGTATGATCAGCAATGAG-----GCGGTGGTCAATATCCTG TCGAGCTCATCACCACCACAGCGG------gatcgcaccactgcactccagctgggcgacagagcgagactccgtgtctcaaaaaaaaaagagtca ggcaactccacagggccatgatgcctgtcctcctcccacacccctcgctgctgccgccgccagattgaccagtctccctccgtcctccccc
                                                                 p1274 for
agAAAAAGGTGCACTGCCTCAACATGGACAGCCCTCTCTTCCAGCCCTCTACCTCAGCCCACACTCCTCCAGCCTCCAACACCATCGAGCCG
                                    Exon 10
GGGCAGCAGAGCTTTGTGCAGtacctggcatgcctgtcacccct------ttcctctccgcctttcttccaccatgactccagagagatgagactc ccagagtcaggagaggacagcctgggtgcacaggagaggagagacagagaaggcattgctcaggacactgacaaggatgtggccctgtcctcct
     p1274 rev
cctctgcccagtacaggtcatgtctttccactgtgaggtctcaggggtgggactcttaattctagccgatatttgaaggcagcaggtgggg
                                        p1391 for
tggggtgaagagcagctgcccatgccgntggccctaccatgccatgccatgcagGTCAGAGTGTCCCCATCCGTCTCCCAGTTCCTGCTCCAGTTAGACAGC
                                                                                     Exon 11
TGCCACCTGGACTTGGGCCTGAGGGAGGCACCGTGAACTCATCCAGGGCCGGGCCAAGGGCCGGGGCGGCCAACTGTGTGAGCCTGCTGTCCCAAGCCCCGA GGGTGACCCGCCGCTTCAGCTTCCTCCTCCACTTCTACACAGTACCCATACCCAAAACCGGACACCCTCAGCTGCACGGTAGCCCTGCGTCCCAAGACCG
```

FIG. 5D

GGTCTCAAGACCAGgtgagtgggcctgggcggccagcttcaagtgggagcttccagtctgtgattgcatgaagggacatggcagcccacaggat gtggccagctgtgaggg-----gatcttccaggactcacccagagcatccagctacgaagcggtggagatggattcaaagccaaggctctaggt gggctggggtcacggagccaggagtaaacctggaagccggctcccaaagtgccacatactgctctctctcttctcctccagGAAGTCCATAGGACTG Exon 12
TCTTCATGCGCTTGAACATCATCAGCCCTGACCTGTCTGgtgagctcccctccagtctctcgggttatctgtgagtcacagtaggcaca gcgggcagccctgagaacggcctggcacatagcacatggcaaggtga-------ccctctaggtgacagtcctagcaaccatgctcaatnncagg cctggctgtgatgagcccgtttgctgcaagagaagactgaggttcagagaagtcgagggtccatggctcagcagagagctggcaccaaaccccacatgggc p1702 for
cagcacaacagggtaggggatggggcaggggcagagtggcagtgctgatggctcggcctctctagGTTGCACAAGCAAAGGCCTCGTCCTGCCCGC Exon 13
CGTGCTGGGGCATCACCTTGGTCCTTCCTCATCGGGGCCTCCTGCACTCTGGTACATCTACTCGCACACGCgtgagtaccccaggcccc

FIG. 5E

```
cacagtgagcatgccgggcccctccatccacccggggagccagtgaagccctctgaaggattaagggcccctggcaggaccctgacctccgccctg
ccccgctcccgctcccagGTTCCCCCAGCCAAGCGGGAGCCCGTGGTGGCTGCCCCCGGCTCCTCCTCGGAGAGCAGCACCAACCACAGCAT
```

Exon 14

```
CGGGAGCACCCAGAGCACCCCCTGCTCCACCAGCAGCATGGCCCCGGCCCCCGGCGCTCGCCCAGCAGGAGAGACTGAGCAGCCGCCAGCTGG
gagcactggtgtgaactcaccctgggagccagtcctccactgaccagtcctcccgcctgtctctccgctaccctgtctccctctcagaggc
ctgctgccagtgcagccactggcttgaacacctggggtccctccacccacagaaccttcaacccagtgggtctggatatgctgccaggagac
agaccactgccacgctgttgtaaaaacccaagtccctgtcatttgacctggatccagctgtgaactgagctgggcaggaaggagaacttgaa
acagattcaggccagccagccaacccagcagccaacagcacctccccgctgggaagaagaagagcccagccaccctgatctatcctgcgcctcc
acacctgaacttgcctaactaactggcagggagacaggagccagcctgggagcccagccagaggtgcaagaacagtgggcgttgggag
acctagctcctgccacatgagccccctcgggcagcccctctgccgtcgggcagcagcagagaggggagtagccaagctgcttgtcctgggcctgccccctgtgtattcac
caccaataatcagaccatgaaacctgaaa
```

FIG. 5F

GENOMIC SEQUENCE ENCODING ENDOGLIN AND FRAGMENTS THEREOF

This application is a continuation of Ser. No. 08/346,129 filed Nov. 29, 1994 now abandoned.

The experimental work reported herein was sponsored in part by National Institutes of Health Grant No. 1 R01 HL 49171-01. The U.S. Government therefore has certain rights in the invention.

BACKGROUND OF THE INVENTION

The field of the invention is diagnosis and genetic therapy for inherited diseases.

Hereditary haemorrhagic telangiectasia (HHT) or Osler-Weber-Rendu disease (OMIM #18730) is an autosomal dominant disorder characterized by multisystemic vascular dysplasia and recurrent haemorrhage. The disorder is named after the recurrent hemorrhage from vascular lesions, especially in the nasal mucosa and gastrointestinal tract, and for the presence of mucosal, dermal and visceral telangiectases. Pulmonary arteriovenous malformations (PAVMs) occur in approximately 20% of patients and are associated with serious complications including stroke and brain abscess. Other neurological manifestations include cerebral arteriovenous malformation, aneurysm and migraine headache.

Ultrastructural analyses of the vascular dysplasia seen in affected individuals have failed to demonstrate a unique pathological abnormality that might suggest the nature of the primary biochemical defect. Studies indicate that the dilated channels of telangiectases are lined by a single layer of endothelium attached to a continuous basement membrane (Jahnke, Arch. Otolaryngol. 91:262–265, 1970; Hashimoto and Pritzker, Oral Surg., Oral Med., Oral Pathol. 34:751–768, 1972). The earliest event in the formation of telangiectases appears to be dilation of post-capillary venules (Braverman et al., J. Invest Dermatol. 95:422–427, 1990). Eventually the dilated venules connect to enlarging arterioles through capillary segments which later disappear, creating direct arteriolar-venular connections. This sequence of events is associated with a perivascular mononuclear infiltrate (Braverman et al., J. Invest Dermatol. 95:422–427, 1990). Various explanations have been put forward to explain the angiodysplasia seen in HHT including endothelial cell degeneration (Manafee et al., Arch. Otolaryngol. 101:246–251, 1975), defects in endothelial junctions (Hashimoto and Pritzker, Oral Surg., Oral Med., Oral Pathol. 34:751–768, 1972), lack of elastic fibers and incomplete smooth muscle cell coating of the vessels (Jahnke, Arch. Otolaryngol. 91:262–265, 1970), and weak connective tissue surrounding the vessel (Manafee et al., Arch. Otolaryngol. 101:246–251, 1975).

Genetic linkage for some HHT families was recently established to markers on chromosome 9q33-q34 (McDonald et al., Nature Genet. 6:197–204, 1994; Shovlin et al., Nature Genet. 6:205–209, 1994) and the locus was named OWR1. Genetic heterogeneity was established with the identification of some families clearly not linked to this region (Shovlin et al., Nature Genet. 6:205–209, 1994). The identification of key obligate recombinants in affected individuals allowed refinement of the OWR1 locus and placed the most likely candidate interval between D9S60 and D9S61 in a 2 centiMorgan (cM) interval (Shovlin et al., Nature Genet. 6:205–209, 1994).

SUMMARY OF THE INVENTION

The present invention is based upon the discovery that various defects in the gene encoding endoglin, a transforming growth factor β (TGF-β) binding protein, are responsible for some cases of HHT. Endoglin is a homodimeric integral membrane glycoprotein expressed at high levels on human vascular endothelial cells of capillaries, arterioles and venules in all tissues examined (Gougos and Letarte, J. Biol. Chem. 265:8361–8364, 1990; and Bellon et al., Eur. J. Immunol. 23:2340–2345, 1993). The cDNA sequence of human endoglin (SEQ ID NO:1) is shown in FIG. 1. In the work discussed herein, the genomic DNA of human endoglin has been cloned, its exon/intron structure determined, and the characteristics of certain HHT-associated mutations ascertained.

Endoglin is the most abundant TGF-βbinding protein on endothelial cells (Cheifetz et al., J. Biol. Chem. 267:19027–19030, 1992). In the presence of TGF-β ligand, endoglin can associate with the two TGF-β signaling receptors RI and RII (Yamashita et al., J. Biol. Chem. 269:1995–2001, 1994). TGF-β is the prototype of a family of at least 25 growth factors which regulate growth, differentiation, motility, tissue remodeling, wound repair and programmed cell death in many cell types (Massague et al., Trends Cell Biol. 4:172–178, 1994, herein incorporated by reference).

The invention features an isolated DNA comprising a human genomic DNA sequence encoding endoglin. The genomic DNA preferably includes a nucleotide sequence corresponding to any one or more of SEQ ID NOs:9–19, and more preferably has the sequence of FIG. 5 (SEQ ID NOs:9–19). By "isolated DNA" is meant a DNA that is not immediately contiguous with at least one of the two genes with which it is immediately contiguous (i.e., one at the 5' end and one at the 3' end) in the naturally-occurring human genome. The term thus encompasses, for example, a genomic DNA fragment produced by PCR or restriction endonuclease treatment, whether such fragment is incorporated into a vector, integrated into the genome of a cell (at a site other than the naturally-occurring site), or independent of any other DNA sequences. The DNA may be double-stranded or single-stranded, sense or antisense.

Also within the invention is a single-stranded oligonucleotide 14–50 nucleotides in length having a nucleotide sequence identical to that of a portion of a strand of a human endoglin gene, which portion is within an intron of the gene and preferably borders an adjacent exon. Such an oligonucleotide can be paired with a second single-stranded oligonucleotide also 14–50 nucleotides length which is identical to a fragment of the strand complementary to the first strand (i.e., where the first strand is the sense strand, the second strand would be the antisense strand, and vice versa), which fragment is within (a) a second intron, (b) the 5' untranslated region immediately adjacent to the translation start signal, or (c) the 3' untranslated region immediately adjacent to the termination signal of the gene. The pair of oligonucleotides could serve as PCR primers selected to prime the PCR amplification of a single exon of the gene, or up to three exons (with intervening introns).

Described herein is a diagnostic method useful for determining whether a patient or a fetus bears a gene that would make the patient or fetus susceptible to HHT. This method includes the steps of obtaining a sample of genomic DNA from the patient (e.g., in the form of a blood sample) or fetus (e.g., by amniocentesis or chorionic villi sampling), and determining whether the DNA contains a mutation in a gene encoding endoglin, betaglycan, TGF-β type I receptor (RI), TGF-β type II receptor (RII), or TGF-β/activin type I receptor (TSR-I), such a mutation being an indication that the patient or fetus bears a gene making the patient or fetus susceptible to HHT. The method may include the step of treating the sample of genomic DNA with a restriction enzyme (e.g., MaeIII, where the gene of interest is endoglin). Alternatively or in addition, the method may include the step of subjecting the sample to PCR, using (1) a forward PCR primer complementary to a portion of the antisense strand of the gene, such portion being within (a) a first intron of said gene, or (b) the 5' untranslated region adjacent to the start codon of the gene; and (2) a reverse PCR primer complementary to a fragment of the sense strand of the gene, such fragment being within (a) a second intron of the gene, or (b) the 3' untranslated region adjacent to the termination codon of the gene.

Another diagnostic method of the invention includes the steps of identifying an individual suspected of being genetically predisposed to developing the HHT phenotype; obtaining from that individual a sample of mRNA from a tissue (e.g., the vascular endothelial cells of a newborn's placenta or umbilical cord) which normally expresses a gene of the TGF-β receptor complex; subjecting the mRNA to RT-PCR to produce amplified cDNA having a sequence corresponding to that of a portion of the mRNA of the gene of interest; and determining whether the amplified cDNA includes a mutation responsible for the HHT phenotype, the presence of such a mutation being an indication that the individual is genetically predisposed to developing the HHT phenotype.

The invention also includes compositions and methods for treating or preventing the symptoms of HHT by means of genetic therapy. Such a method would include the steps of identifying a patient who has inherited a defective gene that encodes a component of the TGF-β receptor complex (e.g., endoglin); and introducing into the vascular endothelial cells of the patient an isolated DNA encoding that component, operably linked to an expression control sequence for expression in endothelial cells. The isolated DNA is preferably within (a) a vector suitable for introducing DNA into endothelial cells, or (b) liposomes suitable for introducing DNA into endothelial cells, and can include the endoglin cDNA sequence of SEQ ID NO:1 or a degenerate variant thereof. The DNA may be introduced into the patient by intravenous injection or by intravenous catheter.

One could alternatively treat HHT by increasing the amount of TGF-β available at the cell surface, to counteract the resistance of the vascular endothelial cells to TGF-β attributable to a malfunctioning TGF-β receptor complex. This could be accomplished by applying a pharmaceutical preparation containing TGF-β (preferably ⊕1 or β3) to the skin or mucous membrane at the site of a telangiectasis (e.g., in the patient's nose), or by injection.

The invention further encompasses an animal model for HHT, such as a non-human transgenic animal (e.g., a rodent such as a mouse or rat) bearing a transgene encoding an inactive, mutant form of endoglin; a mouse, each of the cells of which has only one allele encoding wildtype murine endoglin; or a mouse which has no allele encoding wildtype murine endoglin.

Other features and advantages of the invention will be apparent from the detailed description that follows, and from the claims.

BRIEF DESCRIPTION OF THE DRAWINGS

FIGS. 1A, 1B, and 1C together represent the genomic structure of endoglin. The cDNA sequence of endoglin (SEQ ID NO: 1) is shown with the deduced amino acid sequence (SEQ ID NO:2) below. The nucleotide and amino acid positions are based on numbering the "A" in the ATG start codon of the full-length L-form of endoglin (Bellon et al., Eur. J. Immunol. 23:2340–2345, 1993) as nucleotide number 1. Exons 1 through 14 are labelled above the cDNA sequence in bold and the intron/exon borders are marked with arrows. Exon 7 codes for amino acids 273–331; exon 11 spans residues 477–562. The four potential N-linked glycosylation sites are in boldface, italicized type and are underlined. The membrane spanning domain is double underlined. The positions of the mutations described in this report are shown in relation to the gene structure; the C to G change at nucleotide 831 is indicated by a star and the positions of the two deletions are underlined (nucleotides 882–920 and 1553–1554). The two basepair deletion creates a premature termination codon, which is indicated by bold type.

FIG. 2c is a comparison of the normal (SEQ ID NO:3) and mutant (SEQ ID NO:4) DNA and amino acid sequences in the region of the mutation in sample 1159. This C to G substitution converts a tyrosine to a stop codon at amino acid 277.

FIG. 3a is a comparison of the normal (SEQ ID NO:5) and mutant (SEQ ID NO:6) DNA and amino acid sequences in the region of the deletion mutation in sample 8019 from the 9q3-linked Family 3186. This 39 bp deletion, which is located at nucleotide positions 882 through 920 in exon 7, removes 13 amino acids from the protein and alters the first amino acid (position 307) in a potential N-linked glycosylation site.

FIG. 4c is a representation of the normal (SEQ ID NO:7) and mutant (SEQ ID NO:8) DNA and amino acid sequences in the region of the 2 bp deletion in sample 2061. The two deleted nucleotides are underlined in the normal sequence. This mutation causes a frameshift and a premature termination after an additional seven amino acids.

FIGS. 5A, 5B, 5C, 5D, 5E, and 5F together depict a partial genomic DNA sequence of the wildtype human endoglin gene (SEQ ID NOs:9–19). Capital letters indicate coding sequence (exons), while lower-case letters indicate introns. Dashes indicate portions of the introns for which the nucleotide sequence has not yet been determined.

DETAILED DESCRIPTION

Figure 2A:
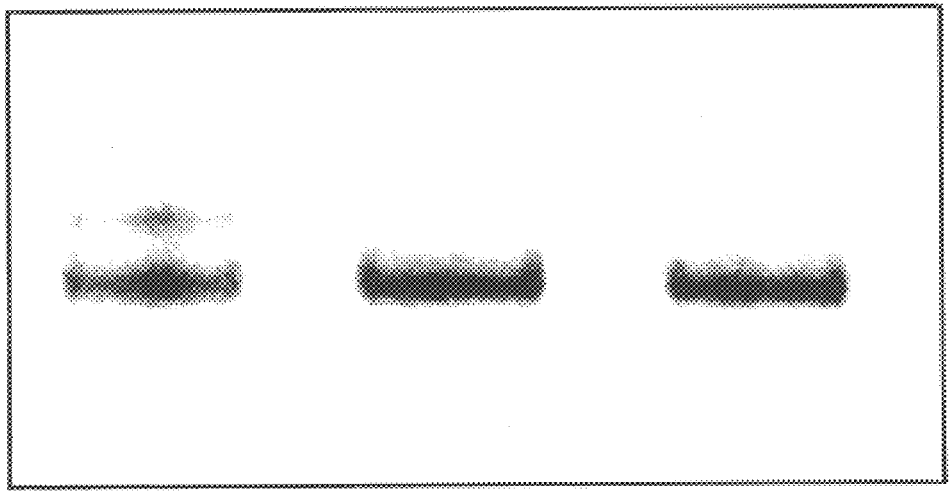
FIG. 2a is an heteroduplex analysis showing. a shift in an affected proband (sample 1159; lane 1) next to two samples (lanes 2 and 3) not displaying this anomaly.

The endoglin gene previously was mapped to human chromosome 9q34 using fluorescence in situ hybridization (FISH) (Fernandez-Ruiz et al., Cytogenet. Cell Genet. 64:204–207, 1993).

Genomic Structure of Endoglin

As an initial screen for gross abnormalities in the endoglin gene in affected HHT individuals, Southern blots of DNA from the probands of 33 unrelated families having family members with HHT were probed with a nearly complete cDNA of endoglin, the clone 18A of Gougos and Letarte, supra. This analysis using three restriction endonucleases revealed no gross abnormalities of the endoglin gene in these samples. Reverse transcription-PCR (RT-PCR) was attempted using RNA prepared from several Epstein-Barr virus-transformed lymphoblast lines established from our patient cohort, but expression levels of endoglin appeared to be too low to allow routine amplification in a single round (35 cycles) of PCR. As the expression of endoglin is restricted to endothelial cells, activated monocytes (Lastres et al., Eur. J. Immunol. 22:393–397, 1992), syncytiotrophoblast (Gougos et al., Int. Immunol. 4:83–92, 1992), and certain stromal cells (St. Jacques et al., Endocrinology 134:2645–2657, 1994), screening for mutations within endoglin cDNA was not feasible. The genomic structure of endoglin was therefore studied.

A gridded cosmid chromosome 9 library was screened with the 18A cDNA probe, and 17 cosmids were obtained. Southern analysis of these clones in comparison with total genomic DNA revealed that one cosmid, 21c10, appeared to contain most of the gene. This cosmid was subcloned into a phagemid library which was screened for positive plaques with the 18A cDNA probe. Hybridizing clones were converted to plasmids and sequenced using vector primers flanking the cloning site to identify intron-exon borders.

Preliminary sequence analysis suggests that the coding region of endoglin contains 14 exons (FIG. 1). One or more splice junctions may remain unidentified within the 5' end of the gene, as the sequence denoted exon 1, which contains the putative signal peptide, was found to be missing in the 21c10 cosmid. There is also evidence for alternative splicing variants of the endoglin transcript. Since only one variant was used to identify subclones for genomic sequencing, it is possible that additional exons exist within the depicted coding region (FIG. 1). (The exon number assignments must be regarded as preliminary until the entire gene structure is resolved.)

The 14 exons are sufficiently small to allow for PCR amplification of each as a single unit (Table 1). The smallest is exon 12 which contains the complete membrane spanning domain and is 55 basepairs (bp) in length. The longest exon completely contained within the coding region is exon 11 (258 bp). Exon 14 contains at least 429 bp but contains only 125 bases of coding information, the remainder being the 3' untranslated region.

TABLE 1

PCR assays for endoglin exons

| Exon | Size (bp) | Forward Primer Sequence (5' –> 3') | Reverse Primer Sequence (5' –> 3') | PCR Prod. Size | Buffer | [MgCl2] | Annealing Temp | # of cycles |
|---|---|---|---|---|---|---|---|---|
| 1 | >67 | | | | | | | |
| 2 | 152 | cctcataaggtggctgtgatgatg SEQ ID NO: 20 | catctgccttggagcttcctct SEQ ID NO: 21 | 413 | BMB | 1.5 mM | 60° | 35 |
| 3 | 141 | | | | | | | |
| 4 | 163 | ttcctgacctcctacatgg SEQ ID NO: 22 | ctcttggtgcccaagttt SEQ ID NO: 23 | 330 | TNK 50 | 1.0 mM | 51° | 30 |
| 5 | 166 | cgggctctgttaggtgcag SEQ ID NO: 24 | gggtggggcttataaggga SEQ ID NO: 25 | 294 | TNK 25 | 1.0 mM | 57° | 35 |
| 6 | 127 | ctgtccgcttcagtgttccatc SEQ ID NO: 26 | ggaaacttccctgatccagaggtt SEQ ID NO: 27 | 230 | TNK 100 | 1.5 mM | 59° | 40 |
| 7 | 176 | gaggcctggcataaccct SEQ ID NO: 28 | gtggccactgatccaagg SEQ ID NO: 29 | 315 | BMB | 1.5 mM | 60° | 35 |
| 8 | 141 | acacatatcacacagtgaccagc SEQ ID NO: 30 | ctaggggaggaaccagatgtc SEQ ID NO: 31 | | TNK 50 | 1.0 mM | 55° | 30 |
| 9 | 178 | | | | | | | |
| 10 | 117 | agattgaccaagtctccctccc SEQ ID NO: 32 | aggctgtctccctcctgactct SEQ ID NO: 33 | 227 | TNK 50 | 1.0 mM | 61° | 35 |
| 11 | 258 | actcaggggtgggaactctt SEQ ID NO: 34 | ccttccatgcaaaccacag SEQ ID NO: 35 | 430 | TNK 50 | 1.0 mM | 57° | 32 |
| 12 | 55 | gagtaaacctggaagccgc SEQ ID NO: 36 | gccactagaacaaacccgag SEQ ID NO: 37 | 164 | TNK 100 | 1.0 mM | 55° | 35 |
| 13 | 111 | ccagcacaacagggtaggggat SEQ ID NO: 38 | ctcagaggcttcactgggctcc SEQ ID NO: 39 | 255 | TNK 50 | 1.0 mM | 61° | 35 |
| 14 | >429 | tgaagcctctgagggattgagg SEQ ID NO: 40 | gagttcacaccagtgctcccag SEQ ID NO: 41 | 267 | TNK 50 | 1.0 mM | 57° | 40 |

Identification of HHT Mutations

In an initial screen for mutations, primers located within the introns flanking exons 7 and 11 (the first exons to be identified) were designed to establish PCR assays for each exon (see Methodology). A panel of 68 DNA samples was used for the mutation screen. These were collected from probands of unrelated families, most of which were members of kindreds with PAVM involvement, increasing the likelihood that the individuals would harbour mutations at the OWR1 locus. Included in our analysis was one member from each of eight 9q3-linked families previously described (McDonald et al., Nature Genet. 6:197–204, 1994). Heteroduplex analysis was performed on amplified products from this cohort as a screen for potential mutations. Abnormal PCR products seen on these gels were directly sequenced for further analysis.

Figure 2B:
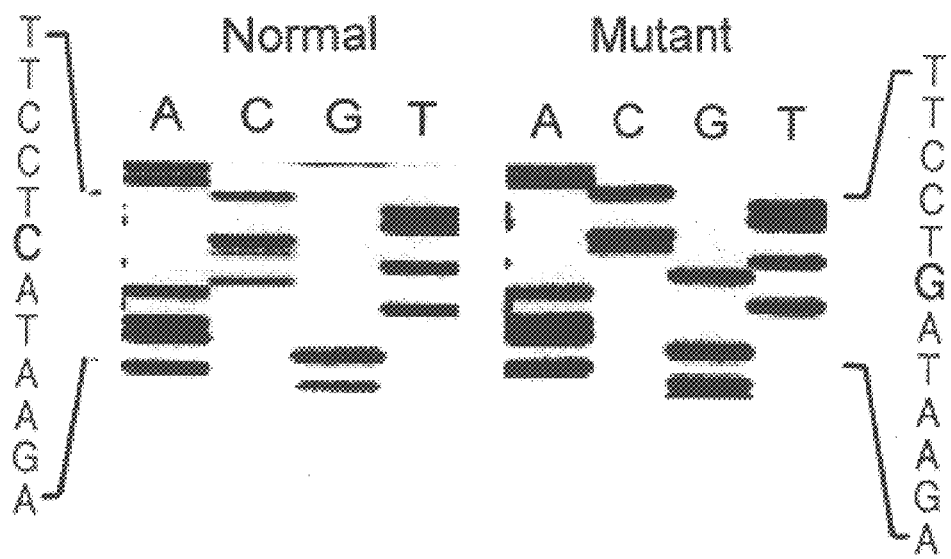
FIG. 2b is a photograph of a sequencing gel comparing the sequences of representative clones revealing the normal (C) and mutant sequence (G) of amplified exon 7 in sample 1159.

With this initial screen, three mutations in affected individuals were identified. The first mutation was identified by a heteroduplex shift in the exon 7 PCR product from sample 1159 (FIG. 2a). The products of two independent PCR reactions were directly sequenced, whereupon a C (normal) and a G (mutation) at nucleotide position 831 were clearly visible. PCR products amplified from this individual were then cloned and individual clones sequenced to validate the results of the direct sequencing (FIG. 2b). This change converts a tyrosine at codon 277 to a termination codon (FIG. 2c). This mutation is present in the proband of a pedigree with multiple affected members having documented PAVMs. However, additional members of this family were not available for analysis. The truncated protein resulting from this mutation would comprise only half of the extracellular domain and lack the membrane spanning and cytoplasmic domains.

Figure 3B:
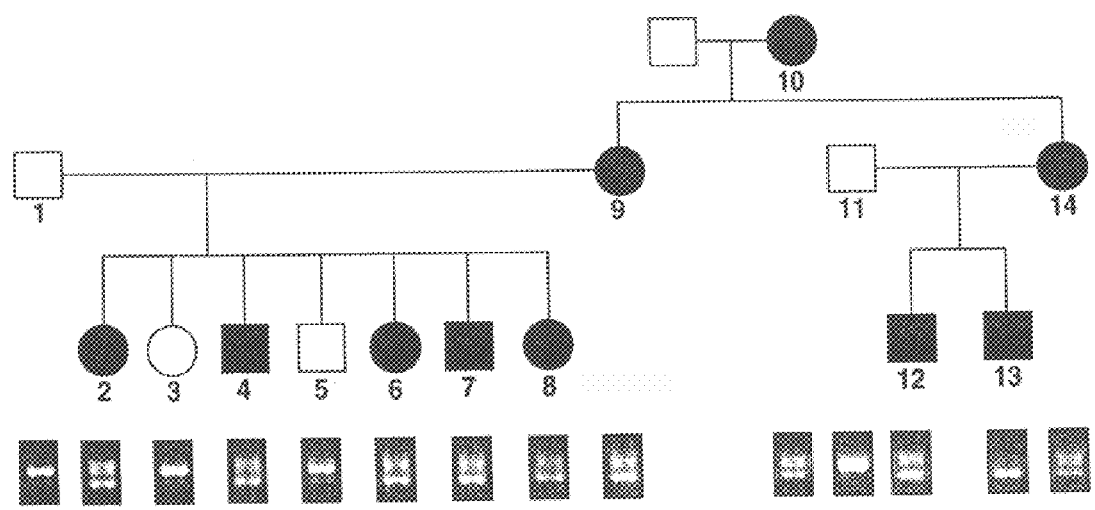
FIG. 3b is an illustration of the inheritance of HHT by the members of Family 3186, showing segregation of the 39 bp deletion. Agarose gel analysis of amplified exon 7 from each member of Family 3186 reveals the presence of a lower band (the 39 bp deletion product) in affected family members only. Preferential amplification of the smaller fragment is sometimes observed (see individual 13).

Amplification of exon 7 in sample 8019 revealed a second mutation, in a family (Family 3186) previously linked to 9q3. A second PCR fragment smaller than the wild-type fragment was visible in both agarose gels and heteroduplex analysis, suggesting the existence of a deletion. The smaller fragment was not seen in 278 normal chromosomes and is unlikely to be a polymorphism. Sequence analysis of the PCR products revealed a 39 bp deletion in the exon beginning at nucleotide position 882 of endoglin (FIG. 3a). This in-frame deletion removes 13 amino acids (amino acids 295 to 307) and alters the first amino acid of a potential N-linked glycosylation site (see FIG. 1). Amplification of this exon revealed the presence of the deletion in all affected family members, but no unaffected members (FIG. 3b).

Figure 4A:
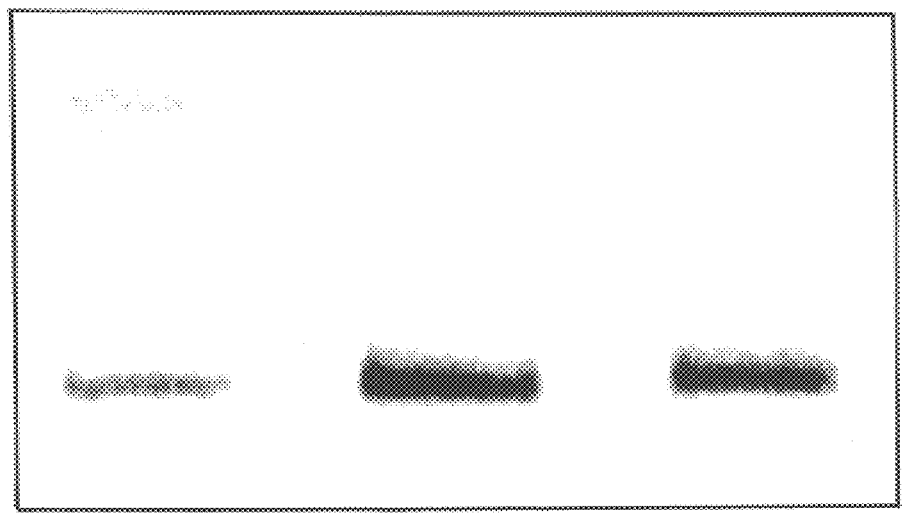
FIG. 4a is an heteroduplex analysis of sample 2061 showing a shift in an affected proband (sample 2061; lane 1) next to two samples (lanes 2 and 3) not displaying this anomaly.
Figure 4B:
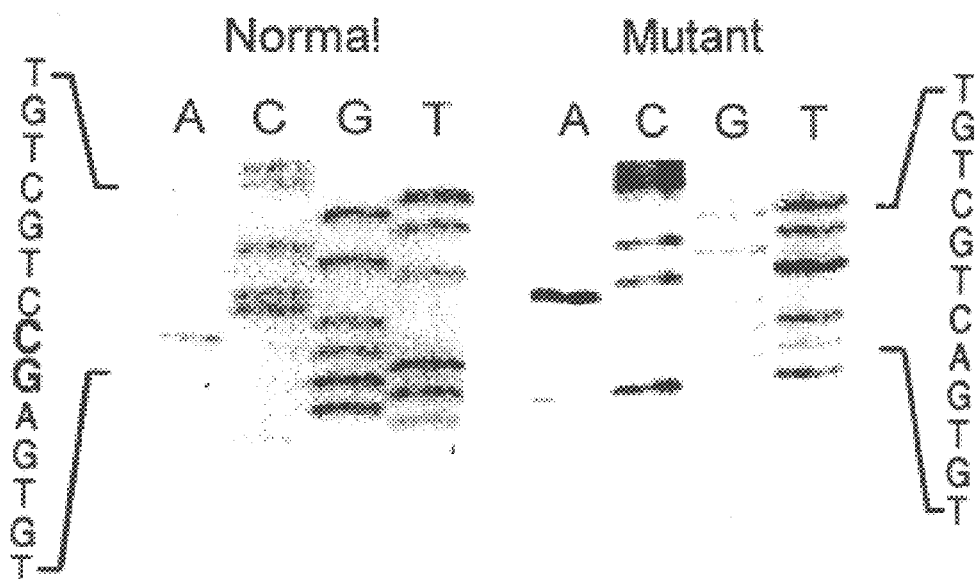
FIG. 4b is a photograph of gels indicating the sequence of the 2 bp deletion in sample 2061, compared to the normal sequence. The sequences of the two independently cloned PCR products of affected individual sample 2061 reveal the normal sequence and the 2 bp deletion in exon 11 beginning at nucleotide position 1553.
Figure 4D:
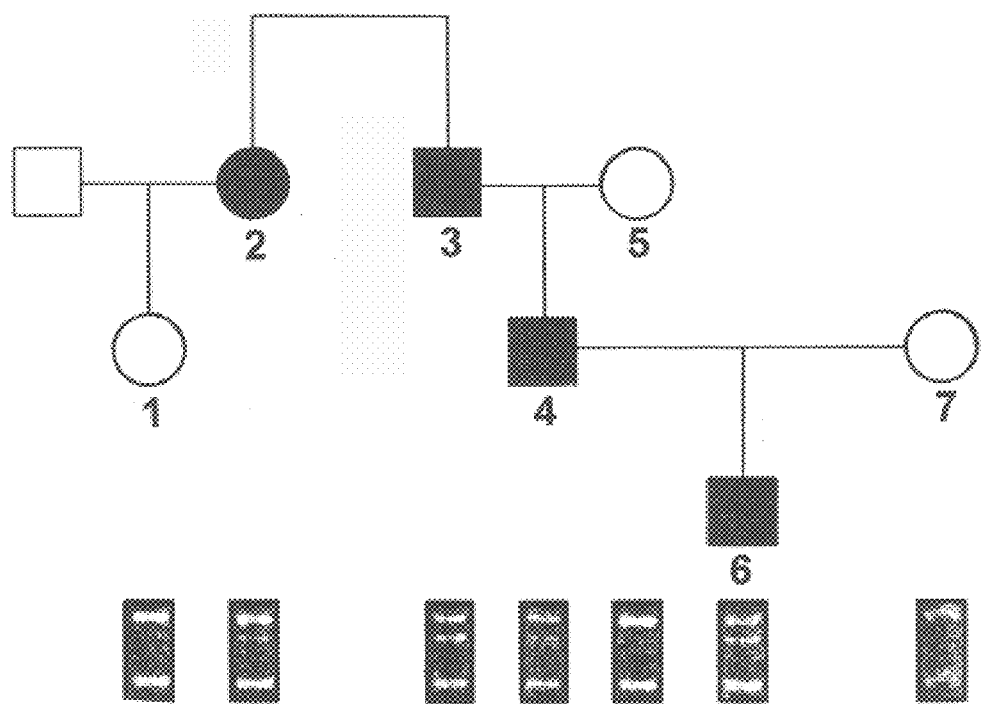
FIG. 4d is an illustration of the inheritance of HHT by the members of Family 63, and an agarose gel electrophoresis analysis of amplified exon 11 from each family member, showing segregation of the 2 bp deletion. The 2 bp deletion creates an additional MaeIII restriction site. Affected family members exhibit an additional novel fragment visible as the middle band in each lane, with half the intensity of the other two bands. A second novel band produced by digestion at this site is not visible on this gel.

Heteroduplex analysis of amplified exon 11 revealed a very pronounced band in sample 2061 that was not visible with agarose gel electrophoresis (FIG. 4a). Independent clones of the PCR product were sequenced, revealing the wild-type sequence and a 2 bp deletion beginning with nucleotide 1553 of endoglin (FIG. 4b). This deletion creates a MaeIII restriction site. This sample was from the proband of a family with multiple affected members displaying PAVMs. Exon 11 was amplified from all available family members and digested with MaeIII. All affected family members share the additional MaeIII site, whereas the unaffected members do not, establishing linkage of this mutation to the disease phenotype in this family (FIG. 4d). The mutation creates a frame shift that results in a premature termination codon 8 amino acids beyond the deletion (FIG. 4c). The predicted truncated protein would lack the membrane spanning and cytoplasmic domains of endoglin.

Discussion

These results, in which three independent mutations in affected HHT individuals are identified, establish the endoglin gene as the HHT1 disease locus mapping to 9q3. The gene maps to the tightest HHT1 candidate interval on 9q33–q34, based on evidence from the mouse and human genetic and physical maps. The restricted tissue distribution of endoglin and its expression at high levels on the surface of endothelial cells is consistent with the pathology of the disorder. Two of the three mutations described in this report create premature termination codons and would be expected to lead to reduced message levels that if translated would encode severely truncated proteins, suggestive of loss-of-function alleles. The third would remove 13 amino acids from the extracellular domain of endoglin and could have a deleterious effect on receptor function. Finally, a defect in a cell surface TGF-β binding protein would account for the limited and localized nature of the vascular lesions present in this disease.

TGF-β in vivo is a potent angiogenic factor and a mediator of vascular remodelling as it controls extracellular matrix production by endothelial cells, smooth muscle cells and pericytes (Madri et al., *Endothelial cell dysfunctions* (eds. Simionescu & Simionescu) (Plenum Press, New York, 1992). Following soft tissue injury or in response to angiogenic factors, microvascular endothelial cells detach from their basement membrane, migrate and proliferate in the interstitial stroma, and form new microvessels. When grown in vitro in three-dimensional gels and in the presence of TGF-β, these endothelial cells form tube-like cellular aggregates with a lumen and tight junctions, and deposit an organized basement membrane, mimicking vessel formation (Madri et al., supra). However, TGF-β, almost exclusively in the β1 isoform, will inhibit the proliferation of endothelial cells grown on plastic (Madri et al., supra; Jennings et al., J. Cell Physiol. 137:167–172, 1988). The response of endothelial cells to TGF-β depends on the interaction with the surrounding extracellular matrix via integrins expressed on their surface (Luscinkas et al., FASEB J. 8:929–938, 1994). The production of matrix protein by stromal interstitial cells, smooth muscle cells, pericytes and endothelial cells and the expression of integrins on endothelial cells are also regulated by TGF-β (Madri et al., supra; Luscinkas et al., FASEB J. 8:929–938, 1994).

Endothelial cells lacking endoglin may respond poorly to TGF-β1 and thus form abnormal blood vessels, particularly in response to injury. TGF-β signalling is mediated by TGF-β receptors RI and RII, which form a heterometric complex upon binding TGF-β (Wrana et al., Cell 71:1003–1014, 1992; Wrana et al., Nature 370:341–347, 1994). Endoglin, which binds TGF-β1 and -p3 with high affinity but does not bind -β2 (Chelfetz et al., J. Biol. Chem. 267:19027–19030, 1992), is structurally related to betaglycan, which binds all three isoforms of TGF-β (Lopez-Casillas et al., Cell 67:785–795, 1991; Wang et al., Cell 67:797–805, 1991). Betaglycan in the presence of ligand interacts with the signaling kinase complex of RI and RII and potentiates the response to all three isoforms of the growth factor (Lopez-Casillas et al., Cell 73:1435–1444, 1993). Endoglin also interacts with the kinase complex, suggesting a potentiating role similar to that of betaglycan. Endothelial cells express very low levels of betaglycan, which may explain their poor response to TGF-β2 (Chelfetz et al., J. Biol. Chem. 265:20533–20538, 1990). Thus endoglin-deficient endothelial cells, as observed in HHT1-linked patients, would express only the signaling RI and RII complex and would lack the regulatory co-receptor capable of controlling the response. This might alter cell adhesion properties, leading to the vascular anomalies seen in this disorder. Stromal cells in several tissues (St. Jacques et al., Endocrinology 134:2645–2657, 1994) and activated monocytes (Lastres et al., Eur. J. Immunol. 22:393–397, 1992) also express endoglin and could be impaired in their response to TGF-β1 in the vascular lesions of HHT1 patients.

As HHT is a genetically heterogenous disease, the observation that endoglin is defective in HHT1-linked families suggests that defects in loci encoding other components of the TGF-β ligand-receptor complex might explain the locus heterogeneity. Before determining the genomic structure of endoglin for mutation analysis, genetic linkage analysis on three non-9q3-linked families was performed, using genetic markers located near the map positions of the TGF-β ligands (β1, β2 and β3) and the only other mapped TGF-β receptor, the TGF-β type II receptor. Inheritance of HHT in one of these families was found to be linked to 3p22, where the TGF-β type II receptor is located (Mathew et al., Genomics 20:114–115, 1994). This supports the hypothesis that the locus heterogeneity in this disorder is be due to mutations within other members of the TGF-β receptor complex or other endothelial cell components of the TGF-β signal transduction pathway.

Methodology

Clinical evaluation. The diagnostic criteria used for collection of family members was as described (McDonald et al., Nature Genet. 6:197–204, 1994).

Genomic sequence determination. A nearly complete cDNA sequence of endoglin (18A) was used to screen a gridded chromosome 9 cosmid library (Los Alamos National Laboratory). One subclone that contained nearly all hybridizing bands that are seen with genomic DNA was subcloned using Lambda ZAP Express system (Stratagene). Plaque screens were performed by hybridization with the 18A cDNA probe to identify positive clones. Intron-exon borders were identified by sequencing these clones using the Sequence Ver. 2.0 DNA sequencing kit (United States Biochemical) using both vector and exon primers.

PCR amplification on exons. Primers were designed from intron genomic sequences flanking exons 7 and 11 of endoglin. For exon 7 (nts 817–992), the forward primer is 5'-GAGGCCTGGCATAACCCT (SEQ ID NO:28), and the reverse primer is 5'-GTGGCCACTGATCCAAGG (SEQ ID NO:29). The 315 bp product was amplified using a buffer consisting of 10 mM Tris-HCl, pH 8.3; 1.5 mM $MgCl_2$; and 50 mM KCl. After initial denaturation, 35 cycles of the following program were run: 94° C. for 30 s; 60° C. for 60 s; 72° C. for 30 s. For exon 11 (nts 1429–1686), the forward primer is 5'ACTCAGGGGTGGGAACTCTT (SEQ ID NO:34) and the reverse is 5'-CCTTCCATGCAAACCACAG (SEQ ID NO:35). The 430 bp product was amplified in 10 mM Tris-HCl , pH 8.3; 1 mM $MgCl_2$; 50 mM KCl; and 5 mM $NH_4Cl$. After initial denaturation, 32 cycles of the following program were run: 94° C. for 50 s, 57° C. for 60 s, 72° C. for 30 s.

Each exon can be amplified using conditions described in Table 1. The amplification reaction contains 100 ng of genomic DNA, 100 ng of each oligonucleotide primer, 0.20 mM of each dNTP, and 1.25 U of Taq DNA polymerase in final volume of 25 μl Reaction conditions were optimized individually for each primer pair by adjusting annealing temperatures and buffer conditions as described (Blanchard et al., PCR Meth. Applic. 2:234–240, 1993), using the Taq polymerase buffer supplied by Boehringer Mannheim Biochemicals, Indianapolis, Ind. (BMB).

Mutation analysis. Heteroduplex analysis was carried out as described using MDE gel mix (AT Biochem) with the addition of 15% urea. Samples were denatured for 5 min and allowed to slow cool before fragments were separated by electrophoresis on non-denaturing gels. Products were visualized by ethidium bromide staining. Altered PCR products detected by heteroduplex analysis were directly sequenced using AmpliTaq Cycle sequencing kit (Perkin Elmer). Primers were end-labelled and samples run on 6% polyacrylamide gels. PCR products of the individuals containing the identified stop codon and the 2 bp deletion were cloned into pCR-Script Direct SK(+) cloning vector using pCR-Script Direct SK(+) Directional Cloning Kit (Stratagene) and sequenced using Sequenase Ver. 2.0 (United State Biochemical).

EXAMPLE 1

Diagnosis

The discovery that a defect in a component of the TGF-β receptor complex underlies the HHT phenotype means that individuals (in particular, those with a family history of the disease) can be tested for inheritance of the disease gene even before symptoms appear. This will permit appropriate genetic counseling of those individuals who have inherited the disease. In addition, individuals diagnosed with the genetic defect can be closely monitored for the appearance of symptoms, permitting early intervention, including genetic therapy, as appropriate. Analysis can be carried out on any suitable genomic DNA sample from the individual to be tested. Typically, a blood sample from an adult or child, or a sample of placental or umbilical cord cells of a newborn would be used; alternatively, one could utilize a fetal sample obtained by amniocentesis or chorionic sampling.

It is expected that standard genetic diagnostic methods can be used. For example, PCR (polymerase chain reaction) can be utilized in the manner described above, to identify the presence of a deletion, addition, or replacement of one or more nucleotides within any one of the exons of endoglin, RI, RII, or betaglycan. Following the PCR reaction, the PCR product can be analyzed by methods as described above, such as the heteroduplex detection technique based upon that of White et al. (Genomics 12:301–306, 1992), or by techniques such as cleavage of RNA-DNA hybrids using RNase A (Myers et al., Science 230:1242–1246, 1985); single-stranded conformation polymorphism (SSCP) analysis (Orita et al., Genomics 10:298–299, 1989); and denaturing gradient gel electrophoresis (DGGE; Myers et al., Methods Enzymol. 155:501–527, 1987). The PCR may be carried out using a primer which adds a G+C-rich sequence (termed a "GC-clamp") to one end of the PCR product, thus improving the sensitivity of the subsequent DGGE procedure (Sheffield et al., Proc. Natl. Acad. Sci. USA 86:232–236, 1989). If the particular mutation present in the patient's family is known to have removed or added a restriction site, or to have significantly increased or decreased the length of a particular restriction fragment, a protocol based upon restriction fragment length polymorphism (RFLP) analysis (perhaps combined with PCR) may be appropriate. The apparent genetic heterogeneity of the HHT phenotype means that the nature of the particular mutation carried by affected individuals in the patient's family may have to be ascertained (e.g., by methods as described above) prior to attempting genetic diagnosis of the patient. Alternatively, a battery of tests designed to identify any of several mutations known to result in HHT may be utilized to screen individuals without a defined familial genotype. The analysis can be carried out on any genomic DNA derived from the patient, typically from a blood sample.

As discussed above, the genetic defect underlying the HHT phenotype may be in an endoglin gene, or in any of the other components of the TGF-β receptor complex. A given family may harbor a defective gene encoding the type I receptor (Frazen et al., Cell 75:681–692, 1993), type II receptor (Lin et al., Cell 68:775–785, 1992), betaglycan (Wang et al., Cell 67:797–805, 1991; Lopez-Casillas et al., Cell 67:785–795, 1991; Moren et al., Biochem. Biophys. Res. Commun. 189:356–362, 1992), or the type I TGF-β/activin receptor (TSR-I; Attisano et al., Cell 75:671–680, 1993). Mutations in each of these genes may be assayed by methods similar to those described herein. If a given family's particular defect has not yet been characterized, selection of the gene most likely to be the source of the defect may be guided by genetic linkage analysis, using appropriate markers.

Instead of basing the diagnosis of HHT on analysis of the genomic DNA of a patient, one could instead seek evidence of the mutation in the level or nature of the relevant expression products. Unlike genomic DNA-based diagnostic methods, this approach permits detection of defects resulting in a decrease in the level of expression of the affected gene (e.g., endoglin) which do not involve mutations in the coding sequence itself. An analysis of expression requires use of cells that normally express the gene of interest in detectable amounts. For endoglin, that means vascular endothelial cells of capillaries, arterioles and venules, or possibly fibroblasts. A useful source of such cells would be the umbilical cord and/or placenta of a newborn, which could be harvested at birth and stored frozen until needed for the diagnostic tests.

Well-known techniques for analyzing expression include mRNA-based methods, such as Northern blots and in situ hybridization (using a nucleic acid probe derived from the relevant cDNA), and quantitative PCR (as described in St-Jacques et al., Endocrinology 134:2645–2657, 1994). One also could employ polypeptide-based methods, including use of antibodies specific for the polypeptide of interest. These techniques permit quantitation of the amount of expression of a given gene in the tissue of interest, at least relative to positive and negative controls. One would expect an individual who is heterozygous for a genetic defect affecting level of expression of endoglin to show up to a 50% loss of expression of this gene in such a hybridization or antibody-based assay. An antibody specific for the carboxy terminal end would be likely to pick up (by failure to bind to) most or all frame-shift and premature termination signal mutations, as well as deletions of the carboxy terminal sequence. Use of a battery of monoclonal antibodies specific for different epitopes of endoglin would be useful for rapidly screening cells to detect those expressing mutant forms of endoglin (i.e., cells which bind to some endoglin-specific MAbs, but not to others), or for quantifying the level of endoglin on the surface of the cells.

Another type of polypeptide-based assay would measure loss of function. For example, one might determine whether the patient's vascular endothelial cells bind and/or respond to TGF-β in a manner similar to cells from a normal individual. Binding of TGF-β could be measured using a radiolabelled ligand or ELISA (for example, see Cheifetz et al., J. Biol. Chem. 269:1995–2001, 1994), while response to the ligand could be measured by a standard TGF-β biological assay, e.g. as discussed in Madri et al., Annals of the New York Academy of Science 593:243–258, 1990 (herein incorporated by reference). A significant degree of loss of. function (e.g., at least 50%) indicates that the patient bears at least one genetic defect in a gene involved in the TGF-Γ response, and is indicative of HHT. Since endoglin forms homodimers, it may be that one defective endoglin gene acts as a dominant negative mutant, suppressing the activity of the normal allele. If so, the level of functional dimeric endoglin would be something less than 50% of the normal level (e.g., 10–30%), even-though only one allele is defective.

Finally, one could use a protein truncation assay (Heim et al., Nature Genetics 8:218–219, 1994) to screen for any genetic defect which results in the production of a truncated polypeptide instead of the wildtype protein.

EXAMPLE 2

Genetic Therapy

A patient with HHT can be treated by supplying a functional gene encoding the defective component of the TGF-β receptor complex. Following diagnosis to determine which gene of the complex is defective in a given patient, a DNA (e.g., a cDNA) is prepared which encodes the wildtype form of the gene operably linked to expression control elements (e.g., promoter and enhancer) that induce expression in endothelial cells. Examples of such expression control elements include those associated with the genes encoding endoglin; Tie-2 (Schnurch and Risau, Development 119:957–968, 1993); the vascular endothelial growth factor (VEGF) receptor Flk-1 (Millauer et al., Cell 72:835–846, 1993); and the Tek endothelial cell receptor (Dumont et al., Genes & Development 8:1897–1909, 1994). The DNA may be incorporated into a vector appropriate for transforming endothelial cells, such as a retrovirus, adenovirus or adeno-associated virus. Alternatively, one of the many other known types of techniques for introducing DNA into cells in vivo may be used: e.g., liposomes. The presence of the target endothelial cells in the lining of the patient's blood vessels means that the DNA may be administered to the patient by the simple means of intravenous injection, whereupon it should travel throughout the bloodstream and contact essentially all of the patient's vascular endothelial cells. In such a protocol, it is expected that approximately 1 to 100 µg/kg body weight would be an effective amount of cDNA.

One could instead rely on local injections into the surface lesions and catheter-delivered infusions directly into the deeper lesions (e.g., PAVMs), repeating the treatment as necessary to achieve the desired response. The catheter could be coupled with a pair of balloons to trap the infusion in a particular region of the blood vessel until the DNA can enter the endothelial cells at the site of the telangiecstasis. Approximately 1 to 10 molecules of DNA per endothelial cell, or about $10^3$ to $10^6$ per telangiectasis, would be an adequate dose.

EXAMPLE 3

TGF-β Treatment

Because the defect in HHT is attributable to the inability of vascular endothelial cells to respond to TGF-β, it is expected that the function of these cells can be improved by increasing the amount of TGF-β present at the cellular surface. Thus, patients suffering from the symptoms of HHT can be treated with TGF-β, preferably by local injection at the site of the telangiecstasis, or by applying a TGF-β-containing ointment or dressing to the skin or mucous membrane at the site of the lesion. This may be particularly appropriate for treating the frequent nosebleeds which often accompany HHT. Where the genetic defect is in an endoglin gene, TGF-β1 or TGF-β3 may be used.

EXAMPLE 4

Animal Model

A line of transgenic animals (e.g., mice, rats, guinea pigs, hamsters, rabbits, or other mammals) could be produced bearing a transgene encoding a defective form of endoglin which retains the ability to dimerize with the wildtype monomer, but which is biologically inactive and forms inactive dimers. Such a mutant form of endoglin would act as a dominant negative mutant, suppressing the activity of the wildtype alleles and permitting use of the animal as a model system for studying HHT and potential therapy therefor. Standard methods of generating such transgenic animals would be used, e.g. as described in Leder et al., U.S. Pat. No. 4,736,866.

Alternatively, standard methods of producing null mice could be used to generate a mouse which bears one defective and one wildtype allele encoding endoglin. It is expected that such a mouse would be susceptible to developing the symptoms which characterize HHT in humans heterozygous for a mutant endoglin gene, and so would serve as a useful animal model for the disease. If desired, two such heterozygous mice could be crossed to produce offspring which are homozygous for the mutant allele.

Other embodiments are within the following claims.

Deposit of Biological Material

Under the terms of the Budapest Treaty on the International Recognition of the Deposit of Microorganisms for the Purpose of Patent Procedure, deposit of cosmid 21c10 has been made with the American Type Culture Collection (ATCC) of Manassas, Va., USA, where the deposit was given Accession Number 98685.

Applicants' assignees, Duke University and HSC Research & Development Limited Partnership, represent that the ATCC is a depository affording permanence of the deposit and ready accessibility thereto by the public if a patent is granted. All restrictions on the availability to the public of the material so deposited have been irrevocably removed. The material will be available during the pendency of the patent application to one determined by the Commissioner to be entitled thereto under 37 C.F.R. 1.14 and 35 U.S.C. §1.22. The deposited material will be maintained with all the care necessary to keep it viable and uncontaminated for a period of at least five years after the most recent request for the furnishing of a sample of the deposited material, and in any case, for a period of at least thirty (30) years after the date of deposit or for the enforceable life of the patent, whichever period is longer. Applicants acknowledge their duty to replace the deposit should the depository be unable to furnish a sample when requested due to the condition of the deposit.

What is claimed is:

1. An isolated DNA molecule consisting of a human genomic DNA sequence encoding endoglin, which is associated with hereditary haemorrhagic telangiectasia, wherein the human genomic DNA sequence:
   (a) encodes a protein with the amino acid sequence of SEQ ID NO:2 wherein the protein retains one or more biological properties of the endoglin encoded by the DNA contained in cosmid 21c10, which has been deposited with the American Type Culture Collection and assigned Accession Number 98685;
   (b) comprises fourteen exons and their intervening introns, wherein the coding sequence of the genomic sequence comprises SEQ ID NO: 1.

2. A pair of PCR primers comprising a first oligonucleotide 14-50 nucleotides in length having a nucleotide sequence identical to that of a 14-50 nucleotide segment of a first strand of endoglin genomic DNA within the cosmid 21c10, which has been deposited with the American Type Culture Collection and assigned Accession Number 98695, and which encodes a protein with the amino acid sequence of SEQ ID NO: 2, said segment of said first strand of endoglin genomic DNA being within an intron of said genomic DNA, and a second oligonucleotide that has a sequence identical to that of 14–50 nucleotide segment of the strand complementary to said first strand of endoglin genomic DNA, said segment of said complementary strand being within (a) a second intron of the genomic DNA, (b) the 5' untranslated region immediately adjacent to the translation start signal of the genomic DNA, or (c) the 3' untranslated region immediately adjacent to the termination signal of the genomic DNA, provided that said pair of primers is selected to prime the PCR amplification of a single exon of said genomic DNA.

3. A vector comprising the isolated DNA molecule of claim 1.

* * * * *

Disclaimer 6,562,957—Michelle Letarte, Toronto (CA); Douglas A. Marchuk, Chapel Hill, NC (US); Kimberly McAllister, Durham, NC (US). GENOMIC SEQUENCE ENCODING ENDOGLIN AND FRAGMENTS THEREOF. Patent dated May 13, 2003. Disclaimer filed July 17, 2003, by the assignee, HSC Research & Development Limited Partnership (CA); Duke University.

Hereby enters this disclaimer to claims 1-3, of said patent.

*(Official Gazette, October 7, 2003)*

```
                          SEQUENCE LISTING (1) GENERAL INFORMATION:

(iii) NUMBER OF SEQUENCES: 41

(2) INFORMATION FOR SEQ ID NO:1:

(i) SEQUENCE CHARACTERISTICS:
        (A) LENGTH: 2025 base pairs
        (B) TYPE: nucleic acid
        (C) STRANDEDNESS: double
        (D) TOPOLOGY: linear (ii) MOLECULE TYPE: DNA (cDNA)

(ix) FEATURE:
        (A) NAME/KEY:  CDS
        (B) LOCATION:  1..1974

(xi) SEQUENCE DESCRIPTION: SEQ ID NO:1:

ATG GAC CGC GGC ACG CTC CCT CTG GCT GTT GCC CTG CTG CTG GCC AGC        48
Met Asp Arg Gly Thr Leu Pro Leu Ala Val Ala Leu Leu Leu Ala Ser
 1               5                  10                  15

TGC AGC CTC AGC CCC ACA AGT CTT GCA GAA ACA GTC CAT TGT GAC CTT        96
Cys Ser Leu Ser Pro Thr Ser Leu Ala Glu Thr Val His Cys Asp Leu
             20                  25                  30

CAG CCT GTG GGC CCC GAG AGG GGC GAG GTG ACA TAT ACC ACT AGC CAG       144
Gln Pro Val Gly Pro Glu Arg Gly Glu Val Thr Tyr Thr Thr Ser Gln
         35                  40                  45

GTC TCG AAG GGC TGC GTG GCT CAG GCC CCC AAT GCC ATC CTT GAA GTC       192
Val Ser Lys Gly Cys Val Ala Gln Ala Pro Asn Ala Ile Leu Glu Val
     50                  55                  60

CAT GTC CTC TTC CTG GAG TTC CCA ACG GGC CCG TCA CAG CTG GAG CTG       240
His Val Leu Phe Leu Glu Phe Pro Thr Gly Pro Ser Gln Leu Glu Leu
 65                  70                  75                  80

ACT CTC CAG GCA TCC AAG CAA AAT GGC ACC TGG CCC CGA GAG GTG CTT       288
Thr Leu Gln Ala Ser Lys Gln Asn Gly Thr Trp Pro Arg Glu Val Leu
                 85                  90                  95
```

```
CTG GTC CTC AGT GTA AAC AGC AGT GTC TTC CTG CAT CTC CAG GCC CTG        336
Leu Val Leu Ser Val Asn Ser Ser Val Phe Leu His Leu Gln Ala Leu
            100                 105                 110

GGA ATC CCA CTG CAC TTG GCC TAC AAT TCC AGC CTG GTC ACC TTC CAA        384
Gly Ile Pro Leu His Leu Ala Tyr Asn Ser Ser Leu Val Thr Phe Gln
                115                 120                 125

GAG CCC CCG GGG GTC AAC ACC ACA GAG CTG CCA TCC TTC CCC AAG ACC        432
Glu Pro Pro Gly Val Asn Thr Thr Glu Leu Pro Ser Phe Pro Lys Thr
        130                 135                 140

CAG ATC CTT GAG TGG GCA GCT GAG AGG GGC CCC ATC ACC TCT GCT GCT        480
Gln Ile Leu Glu Trp Ala Ala Glu Arg Gly Pro Ile Thr Ser Ala Ala
145                 150                 155                 160

GAG CTG AAT GAC CCC CAG AGC ATC CTC CTC CGA CTG GGC CAA GCC CAG        528
Glu Leu Asn Asp Pro Gln Ser Ile Leu Leu Arg Leu Gly Gln Ala Gln
                165                 170                 175

GGG TCA CTG TCC TTC TGC ATG CTG GAA GCC AGC CAG GAC ATG GGC CGC        576
Gly Ser Leu Ser Phe Cys Met Leu Glu Ala Ser Gln Asp Met Gly Arg
        180                 185                 190

ACG CTC GAG TGG CGG CCG CGT ACT CCA GCC TTG GTC CGG GGC TGC CAC        624
Thr Leu Glu Trp Arg Pro Arg Thr Pro Ala Leu Val Arg Gly Cys His
            195                 200                 205

TTG GAA GGC GTG GCC GGC CAC AAG GAG GCG CAC ATC CTG AGG GTC CTG        672
Leu Glu Gly Val Ala Gly His Lys Glu Ala His Ile Leu Arg Val Leu
        210                 215                 220

CCG GGC CAC TCG GCC GGG CCC CGG ACG GTG ACG GTG AAG GTG GAA CTG        720
Pro Gly His Ser Ala Gly Pro Arg Thr Val Thr Val Lys Val Glu Leu
225                 230                 235                 240

AGC TGC GCA CCC GGG GAT CTC GAT GCC GTC CTC ATC CTG CAG GGT CCC        768
Ser Cys Ala Pro Gly Asp Leu Asp Ala Val Leu Ile Leu Gln Gly Pro
                245                 250                 255

CCC TAC GTG TCC TGG CTC ATC GAC GCC AAC CAC AAC ATG CAG ATC TGG        816
Pro Tyr Val Ser Trp Leu Ile Asp Ala Asn His Asn Met Gln Ile Trp
        260                 265                 270

ACC ACT GGA GAA TAC TCC TTC AAG ATC TTT CCA GAG AAA AAC ATT CGT        864
Thr Thr Gly Glu Tyr Ser Phe Lys Ile Phe Pro Glu Lys Asn Ile Arg
            275                 280                 285

GGC TTC AAG CTC CCA GAC ACA CCT CAA GGC CTC CTG GGG GAG GCC CGG        912
Gly Phe Lys Leu Pro Asp Thr Pro Gln Gly Leu Leu Gly Glu Ala Arg
        290                 295                 300

ATG CTC AAT GCC AGC ATT GTG GCA TCC TTC GTG GAG CTA CCG CTG GCC        960
Met Leu Asn Ala Ser Ile Val Ala Ser Phe Val Glu Leu Pro Leu Ala
305                 310                 315                 320

AGC ATT GTC TCA CTT CAT GCC TCC AGC TGC GGT GGT AGG CTG CAG ACC       1008
Ser Ile Val Ser Leu His Ala Ser Ser Cys Gly Gly Arg Leu Gln Thr
                325                 330                 335

TCA CCC GCA CCG ATC CAG ACC ACT CCT CCC AAG GAC ACT TGT AGC CCG       1056
Ser Pro Ala Pro Ile Gln Thr Thr Pro Pro Lys Asp Thr Cys Ser Pro
        340                 345                 350

GAG CTG CTC ATG TCC TTG ATC CAG ACA AAG TGT GCC GAC GAC GCC ATG       1104
Glu Leu Leu Met Ser Leu Ile Gln Thr Lys Cys Ala Asp Asp Ala Met
            355                 360                 365

ACC CTG GTA CTA AAG AAA GAG CTT GTT GCG CAT TTG AAG TGC ACC ATC       1152
Thr Leu Val Leu Lys Lys Glu Leu Val Ala His Leu Lys Cys Thr Ile
        370                 375                 380

ACG GGC CTG ACC TTC TGG GAC CCC AGC TGT GAG GCA GAG GAC AGG GGT       1200
Thr Gly Leu Thr Phe Trp Asp Pro Ser Cys Glu Ala Glu Asp Arg Gly
385                 390                 395                 400

GAC AAG TTT GTC TTG CGC AGT GCT TAC TCC AGC TGT GGC ATG CAG GTG       1248
Asp Lys Phe Val Leu Arg Ser Ala Tyr Ser Ser Cys Gly Met Gln Val
```

|  |  |  |  |  |  |  |  |  |  |  |  |  |  |  |  |
|---|---|---|---|---|---|---|---|---|---|---|---|---|---|---|---|
|  |  |  | 405 |  |  |  | 410 |  |  |  |  | 415 |  |  |  |
| TCA | GCA | AGT | ATG | ATC | AGC | AAT | GAG | GCG | GTG | GTC | AAT | ATC | CTG | TCG | AGC | 1296 |
| Ser | Ala | Ser | Met | Ile | Ser | Asn | Glu | Ala | Val | Val | Asn | Ile | Leu | Ser | Ser |
|  |  |  | 420 |  |  |  | 425 |  |  |  |  | 430 |  |  |  |
| TCA | TCA | CCA | CAG | CGG | AAA | AAG | GTG | CAC | TGC | CTC | AAC | ATG | GAC | AGC | CTC | 1344 |
| Ser | Ser | Pro | Gln | Arg | Lys | Lys | Val | His | Cys | Leu | Asn | Met | Asp | Ser | Leu |
|  |  |  | 435 |  |  |  | 440 |  |  |  |  | 445 |  |  |  |
| TCT | TTC | CAG | CTG | GGC | CTC | TAC | CTC | AGC | CCA | CAC | TTC | CTC | CAG | GCC | TCC | 1392 |
| Ser | Phe | Gln | Leu | Gly | Leu | Tyr | Leu | Ser | Pro | His | Phe | Leu | Gln | Ala | Ser |
|  |  |  | 450 |  |  |  | 455 |  |  |  |  | 460 |  |  |  |
| AAC | ACC | ATC | GAG | CCG | GGG | CAG | CAG | AGC | TTT | GTG | CAG | GTC | AGA | GTG | TCC | 1440 |
| Asn | Thr | Ile | Glu | Pro | Gly | Gln | Gln | Ser | Phe | Val | Gln | Val | Arg | Val | Ser |
| 465 |  |  |  |  | 470 |  |  |  |  | 475 |  |  |  |  | 480 |
| CCA | TCC | GTC | TCC | GAG | TTC | CTG | CTC | CAG | TTA | GAC | AGC | TGC | CAC | CTG | GAC | 1488 |
| Pro | Ser | Val | Ser | Glu | Phe | Leu | Leu | Gln | Leu | Asp | Ser | Cys | His | Leu | Asp |
|  |  |  |  | 485 |  |  |  |  | 490 |  |  |  |  | 495 |  |
| TTG | GGG | CCT | GAG | GGA | GGC | ACC | GTG | GAA | CTC | ATC | CAG | GGC | CGG | GCG | GCC | 1536 |
| Leu | Gly | Pro | Glu | Gly | Gly | Thr | Val | Glu | Leu | Ile | Gln | Gly | Arg | Ala | Ala |
|  |  |  | 500 |  |  |  |  | 505 |  |  |  |  | 510 |  |  |
| AAG | GGC | AAC | TGT | GTG | AGC | CTG | CTG | TCC | CCA | AGC | CCC | GAG | GGT | GAC | CCG | 1584 |
| Lys | Gly | Asn | Cys | Val | Ser | Leu | Leu | Ser | Pro | Ser | Pro | Glu | Gly | Asp | Pro |
|  |  | 515 |  |  |  |  | 520 |  |  |  |  | 525 |  |  |  |
| CGC | TTC | AGC | TTC | CTC | CTC | CAC | TTC | TAC | ACA | GTA | CCC | ATA | CCC | AAA | ACC | 1632 |
| Arg | Phe | Ser | Phe | Leu | Leu | His | Phe | Tyr | Thr | Val | Pro | Ile | Pro | Lys | Thr |
|  |  | 530 |  |  |  |  | 535 |  |  |  |  | 540 |  |  |  |
| GGC | ACC | CTC | AGC | TGC | ACG | GTA | GCC | CTG | CGT | CCC | AAG | ACC | GGG | TCT | CAA | 1680 |
| Gly | Thr | Leu | Ser | Cys | Thr | Val | Ala | Leu | Arg | Pro | Lys | Thr | Gly | Ser | Gln |
| 545 |  |  |  |  | 550 |  |  |  |  | 555 |  |  |  |  | 560 |
| GAC | CAG | GAA | GTC | CAT | AGG | ACT | GTC | TTC | ATG | CGC | TTG | AAC | ATC | ATC | AGC | 1728 |
| Asp | Gln | Glu | Val | His | Arg | Thr | Val | Phe | Met | Arg | Leu | Asn | Ile | Ile | Ser |
|  |  |  |  | 565 |  |  |  |  | 570 |  |  |  |  | 575 |  |
| CCT | GAC | CTG | TCT | GGT | TGC | ACA | AGC | AAA | GGC | CTC | GTC | CTG | CCC | GCC | GTG | 1776 |
| Pro | Asp | Leu | Ser | Gly | Cys | Thr | Ser | Lys | Gly | Leu | Val | Leu | Pro | Ala | Val |
|  |  |  | 580 |  |  |  |  | 585 |  |  |  |  | 590 |  |  |
| CTG | GGC | ATC | ACC | TTT | GGT | GCC | TTC | CTC | ATC | GGG | GCC | CTG | CTC | ACT | GCT | 1824 |
| Leu | Gly | Ile | Thr | Phe | Gly | Ala | Phe | Leu | Ile | Gly | Ala | Leu | Leu | Thr | Ala |
|  |  |  | 595 |  |  |  |  | 600 |  |  |  |  | 605 |  |  |
| GCA | CTC | TGG | TAC | ATC | TAC | TCG | CAC | ACG | CGT | TCC | CCC | AGC | AAG | CGG | GAG | 1872 |
| Ala | Leu | Trp | Tyr | Ile | Tyr | Ser | His | Thr | Arg | Ser | Pro | Ser | Lys | Arg | Glu |
|  | 610 |  |  |  |  | 615 |  |  |  |  | 620 |  |  |  |  |
| CCC | GTG | GTG | GCG | GTG | GCT | GCC | CCG | GCC | TCC | TCG | GAG | AGC | AGC | AGC | ACC | 1920 |
| Pro | Val | Val | Ala | Val | Ala | Ala | Pro | Ala | Ser | Ser | Glu | Ser | Ser | Ser | Thr |
| 625 |  |  |  |  | 630 |  |  |  |  | 635 |  |  |  |  | 640 |
| AAC | CAC | AGC | ATC | GGG | AGC | ACC | CAG | AGC | ACC | CCC | TGC | TCC | ACC | AGC | AGC | 1968 |
| Asn | His | Ser | Ile | Gly | Ser | Thr | Gln | Ser | Thr | Pro | Cys | Ser | Thr | Ser | Ser |
|  |  |  |  | 645 |  |  |  |  | 650 |  |  |  |  | 655 |  |
| ATG | GCA | TAGCCCCGGC | CCCCGCGCT | CGCCCAGCAG | GAGAGACTGA | GCAGCCGCCA |  |  |  |  |  |  |  |  | 2024 |
| Met | Ala |
| G |  |  |  |  |  |  |  |  |  |  |  |  |  |  |  | 2025 |

(2) INFORMATION FOR SEQ ID NO:2:

(i) SEQUENCE CHARACTERISTICS:
        (A) LENGTH: 658 amino acids
        (B) TYPE: amino acid
        (D) TOPOLOGY: linear (ii) MOLECULE TYPE: protein (xi) SEQUENCE DESCRIPTION:SEQ ID NO:2:

-continued

```
Met Asp Arg Gly Thr Leu Pro Leu Ala Val Ala Leu Leu Leu Ala Ser
 1               5                  10                  15

Cys Ser Leu Ser Pro Thr Ser Leu Ala Glu Thr Val His Cys Asp Leu
                20                  25                  30

Gln Pro Val Gly Pro Glu Arg Gly Val Thr Tyr Thr Thr Ser Gln
            35                  40                  45

Val Ser Lys Gly Cys Val Ala Gln Ala Pro Asn Ala Ile Leu Glu Val
        50                  55                  60

His Val Leu Phe Leu Glu Phe Pro Thr Gly Pro Ser Gln Leu Glu Leu
 65                  70                  75                  80

Thr Leu Gln Ala Ser Lys Gln Asn Gly Thr Trp Pro Arg Glu Val Leu
                85                  90                  95

Leu Val Leu Ser Val Asn Ser Ser Val Phe Leu His Leu Gln Ala Leu
                100                 105                 110

Gly Ile Pro Leu His Leu Ala Tyr Asn Ser Ser Leu Val Thr Phe Gln
            115                 120                 125

Glu Pro Pro Gly Val Asn Thr Thr Glu Leu Pro Ser Phe Pro Lys Thr
            130                 135                 140

Gln Ile Leu Glu Trp Ala Ala Glu Arg Gly Pro Ile Thr Ser Ala Ala
145                 150                 155                 160

Glu Leu Asn Asp Pro Gln Ser Ile Leu Leu Arg Leu Gly Gln Ala Gln
                165                 170                 175

Gly Ser Leu Ser Phe Cys Met Leu Glu Ala Ser Gln Asp Met Gly Arg
                180                 185                 190

Thr Leu Glu Trp Arg Pro Arg Thr Pro Ala Leu Val Arg Gly Cys His
                195                 200                 205

Leu Glu Gly Val Ala Gly His Lys Glu Ala His Ile Leu Arg Val Leu
    210                 215                 220

Pro Gly His Ser Ala Gly Pro Arg Thr Val Thr Val Lys Val Glu Leu
225                 230                 235                 240

Ser Cys Ala Pro Gly Asp Leu Asp Ala Val Leu Ile Leu Gln Gly Pro
                245                 250                 255

Pro Tyr Val Ser Trp Leu Ile Asp Ala Asn His Asn Met Gln Ile Trp
                260                 265                 270

Thr Thr Gly Glu Tyr Ser Phe Lys Ile Phe Pro Glu Lys Asn Ile Arg
                275                 280                 285

Gly Phe Lys Leu Pro Asp Thr Pro Gln Gly Leu Leu Gly Glu Ala Arg
    290                 295                 300

Met Leu Asn Ala Ser Ile Val Ala Ser Phe Val Glu Leu Pro Leu Ala
305                 310                 315                 320

Ser Ile Val Ser Leu His Ala Ser Ser Cys Gly Gly Arg Leu Gln Thr
                325                 330                 335

Ser Pro Ala Pro Ile Gln Thr Thr Pro Pro Lys Asp Thr Cys Ser Pro
            340                 345                 350

Glu Leu Leu Met Ser Leu Ile Gln Thr Lys Cys Ala Asp Asp Ala Met
            355                 360                 365

Thr Leu Val Leu Lys Lys Glu Leu Val Ala His Leu Lys Cys Thr Ile
    370                 375                 380

Thr Gly Leu Thr Phe Trp Asp Pro Ser Cys Glu Ala Glu Asp Arg Gly
385                 390                 395                 400

Asp Lys Phe Val Leu Arg Ser Ala Tyr Ser Ser Cys Gly Met Gln Val
                405                 410                 415

Ser Ala Ser Met Ile Ser Asn Glu Ala Val Val Asn Ile Leu Ser Ser
```

```
              420             425             430
Ser Ser Pro Gln Arg Lys Lys Val His Cys Leu Asn Met Asp Ser Leu
        435             440             445

Ser Phe Gln Leu Gly Leu Tyr Leu Ser Pro His Phe Leu Gln Ala Ser
    450             455             460

Asn Thr Ile Glu Pro Gly Gln Gln Ser Phe Val Gln Val Arg Val Ser
465             470             475             480

Pro Ser Val Ser Glu Phe Leu Leu Gln Leu Asp Ser Cys His Leu Asp
                485             490             495

Leu Gly Pro Glu Gly Gly Thr Val Glu Leu Ile Gln Gly Arg Ala Ala
            500             505             510

Lys Gly Asn Cys Val Ser Leu Leu Ser Pro Ser Pro Glu Gly Asp Pro
        515             520             525

Arg Phe Ser Phe Leu Leu His Phe Tyr Thr Val Pro Ile Pro Lys Thr
    530             535             540

Gly Thr Leu Ser Cys Thr Val Ala Leu Arg Pro Lys Thr Gly Ser Gln
545             550             555             560

Asp Gln Glu Val His Arg Thr Val Phe Met Arg Leu Asn Ile Ile Ser
                565             570             575

Pro Asp Leu Ser Gly Cys Thr Ser Lys Gly Leu Val Leu Pro Ala Val
            580             585             590

Leu Gly Ile Thr Phe Gly Ala Phe Leu Ile Gly Ala Leu Leu Thr Ala
        595             600             605

Ala Leu Trp Tyr Ile Tyr Ser His Thr Arg Ser Pro Ser Lys Arg Glu
    610             615             620

Pro Val Val Ala Val Ala Ala Pro Ala Ser Ser Glu Ser Ser Ser Thr
625             630             635             640

Asn His Ser Ile Gly Ser Thr Gln Ser Thr Pro Cys Ser Thr Ser Ser
                645             650             655

Met Ala (2) INFORMATION FOR SEQ ID NO:3:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..21

(xi) SEQUENCE DESCRIPTION: SEQ ID NO:3:

ACT GGA GAA TAC TCC TTC AAG                                        21
Thr Gly Glu Tyr Ser Phe Lys
 1               5

(2) INFORMATION FOR SEQ ID NO:4:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: DNA (genomic)

(ix) FEATURE:
```

```
            (A) NAME/KEY: CDS
            (B) LOCATION: 1..9

(xi) SEQUENCE DESCRIPTION: SEQ ID NO:4:

ACT GGA GAA TAGTCCTTCA AG                                            21
Thr Gly Glu
  1

(2) INFORMATION FOR SEQ ID NO:5:

(i) SEQUENCE CHARACTERISTICS:
            (A) LENGTH: 57 base pairs
            (B) TYPE: nucleic acid
            (C) STRANDEDNESS: double
            (D) TOPOLOGY: linear (ii) MOLECULE TYPE: DNA (genomic)

(ix) FEATURE:
            (A) NAME/KEY: CDS
            (B) LOCATION: 1..57

(xi) SEQUENCE DESCRIPTION:  SEQ ID NO:5:

CTC CCA GAC ACA CCT CAA GGC CTC CTG GGG GAG GCC CGG ATG CTC AAT      48
Leu Pro Asp Thr Pro Gln Gly Leu Leu Gly Glu Ala Arg Met Leu Asn
  1               5                  10                  15

GCC AGC ATT                                                          57
Ala Ser Ile (2) INFORMATION FOR SEQ ID NO:6:

(i) SEQUENCE CHARACTERISTICS:
            (A) LENGTH: 18 base pairs
            (B) TYPE: nucleic acid
            (C) STRANDEDNESS: double
            (D) TOPOLOGY: linear (ii) MOLECULE TYPE: DNA (genomic)

(ix) FEATURE:
            (A) NAME/KEY: CDS
            (B) LOCATION: 1..18

(xi) SEQUENCE DESCRIPTION: SEQ ID NO:6:

CTC CCA GAT GCC AGC ATT                                              18
Leu Pro Asp Ala Ser Ile
  1               5

(2) INFORMATION FOR SEQ ID NO:7:

(i) SEQUENCE CHARACTERISTICS:
            (A) LENGTH: 39 base pairs
            (B) TYPE: nucleic acid
            (C) STRANDEDNESS: double
            (D) TOPOLOGY: linear (ii) MOLECULE TYPE: DNA (genomic)

(ix) FEATURE:
            (A) NAME/KEY: CDS
            (B) LOCATION: 1..39

(xi) SEQUENCE DESCRIPTION: SEQ ID NO:7:

AAC TGT GTG AGC CTG CTG TCC CCA AGC CCC GAG GGT GAC                  39
Asn Cys Val Ser Leu Leu Ser Pro Ser Pro Glu Gly Asp
  1               5                  10

(2) INFORMATION FOR SEQ ID NO:8:

(i) SEQUENCE CHARACTERISTICS:
```

(A) LENGTH: 36 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..33

(xi) SEQUENCE DESCRIPTION: SEQ ID NO:8:

```
AAC TGT GTG ACT GCT GTC CCC AAG CCC CGA GGG TGA                          36
Asn Cys Val Thr Ala Val Pro Lys Pro Arg Gly
  1               5                  10
```

(2) INFORMATION FOR SEQ ID NO:9:

(i) SEQUENCE CHARACTERISTICS:
        (A) LENGTH: 67 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:9:

```
ATGGACCGCG GCACGCTCCC TCTGGCTGTT GCCCTGCTGC TGGCCAGCTG CAGCCTCAGC         60

CCCACAA                                                                  67
```

(2) INFORMATION FOR SEQ ID NO:10:

(i) SEQUENCE CHARACTERISTICS:
        (A) LENGTH: 555 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:10:

```
AATCCATGGA ACGAATATAA TGATATCACC TCATAAGGTG GCTGTGATGA TGCAGGAAAG         60

CGTTAGCTCA TGTCAAGTCC CTAGGAGACG TTTGGAAAGT AGGAGTCATT GTCATCACCT        120

TATTCTCACC TGGCCTCTTT TCATGTCAAG TCCCTAGGAG ACGTTTGGAA AGTAGGAGTC        180

ATTGTCATCA CCTTATTCTC ACCTGGCCTC TTTTCCGGATG TTCTCCAACA GGTCTTGCAG       240

AAACAGTCCA TTGTGACCTT CAGCCTGTGG GCCCCGAGAG GGGCGAGGTG ACATATACCA        300

CTAGCCAGGT CTCGAAGGGC TGCGTGGCTC AGGCCCCCAA TGCCATCCTT GAAGTCCATG        360

TCCTCTTCCT GGAGTTCCCA ACGGTGAGTG TCCCATGGCA GGGTCGGGTG GGGGCTCAGA        420

GGAAGCTCCA AGGCAGATGG GGTGAGGGGT GCCTTCCTTG TGGCTGTCCC TGGGGCAGTG        480

GCTGAGTCCT CGTTAGCCCC CTGCCAAGAG AGTGATGTGG GCATCTCACA GGGCCCATAA        540

GAGGTGGCAT TTCTA                                                        555
```

(2) INFORMATION FOR SEQ ID NO:11:

(i) SEQUENCE CHARACTERISTICS:
        (A) LENGTH: 141 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:11:

| | |
|---|---:|
| CGGCCCGTCA CAGCTGGAGC TGACTCTCCA GGCATCCAAG CAAAATGGCA CCTGGCCCCG | 60 |
| AGAGGTGCTT CTGGTCTCAG TGTAAACAGC AGTGTCTTCC TGCATCTCCA GGCCCTGGGA | 120 |
| ATCCCACTGC ACTTGGCCTA C | 141 |

(2) INFORMATION FOR SEQ ID NO:12:

(i) SEQUENCE CHARACTERISTICS:
        (A) LENGTH: 495 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:12:

| | |
|---|---:|
| GGCCTCTTTC TCTCAGCCAA TGGGCTGACT CCACAAATTA CTTCCTGACC TCCTACATGG | 60 |
| GATAGAGAGG GCACAGGGCA GGAACAGCGT GCTGAGCCTC CACATGTCTC CCCAGAATTC | 120 |
| CAGCCTGGTC ACCTTCCAAG AGCCCCGGG GTCAACACCA CAGAGCTGCC ATCCTTCCCC | 180 |
| AAGACCCAGA TCCTTGAGTG GGCAGCTGAG AGGGGCCCCA TCACCTCTGC TGCTGAGCTG | 240 |
| AATGACCCCC AGAGCATCCT CCTCCGACTG GGCCAAGGTC AGTTTCCCCA GCAACCTCTC | 300 |
| TGGGCCTCAT GATACTGCTC AGGAGGAATC TGAGCTCCTC TGGCCCACAC CTCAAACTTG | 360 |
| GGCACCAAGA GTGCAGGAGG GGACACGCTG TGCCACAGTT CACATGCCAC AAGCCAGTGC | 420 |
| TGCCTTGGGA CAGTGATGGC TCCTCCACCA AATATCAGAT TGAAGCATGT GGAATATGCC | 480 |
| AGGTTCTGAC CTAAA | 495 |

(2) INFORMATION FOR SEQ ID NO:13:

(i) SEQUENCE CHARACTERISTICS:
        (A) LENGTH: 135 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:13:

| | |
|---|---:|
| TTGGCAGGTA GTGGTGGAAG GGAAGTTCGA ACCTAGGTCC TCTGAGCCTC TCCCCTCTGC | 60 |
| AGCACCGTCC TGCCTGCCCC ACCACTATCT TTGGCTGTGG GTGAGGGCGG GCTCTGTTAG | 120 |
| GTGCAGGGCT GCTGA | 135 |

(2) INFORMATION FOR SEQ ID NO:14:

(i) SEQUENCE CHARACTERISTICS:
        (A) LENGTH: 1410 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:14:

| | |
|---|---:|
| CCCAGGGGTC ACTGTCCTTC TGCATGCTGG AAGCCAGCCA GGACATGGGC CGCACGCTCG | 60 |
| AGTGGCGGCC GCGTACTCCA GCCTTGGTCC GGGGCTGCCA CTTGGAAGGC GTGGCCGGCC | 120 |
| ACAAGGAGGC GCACATCCTG AGGGTCCTGC CGGGCCACTC GGCCGGGTAT GGCTCTCGCC | 180 |
| CCGCCCCTGA CACTAGTCCC CACCCCGAGA GACCACCCCC CTGACCCCCC CCGCCCCCT | 240 |
| CTCCGGTCCC TTATAAAGCC CCACCCCAGT CCCAGACCCA GCCCCGCCGC AGCCCTGTGA | 300 |

```
GAGCACAGTC GCTTTCTCCT ACTCTAGGCT ACGCCCCCTA TGGGCCCCTT CCCTTTGGGC    360

ACAAGCCTGG CCCCAGTCCC ATCCCTATCC CATAAACCCA CACCTGGCCA GGTAAGAGTG    420

CAGCCGCCGC CCACCCGACG CCAGGCCTCG CTCCCCGCCT GGCCTGTCCG CTTCAGTGTT    480

CCATCCGTGT TCCCCGCAGG CCCCGGACGG TGACGGTGAA GGTGGAACTG AGCTGCGCAC    540

CCGGGGATCT CGATGCCGTC CTCATCCTGC AGGGTCCCCC CTACGTGTCC TGGCTCATCG    600

ACGCCAACCA CAACATGCAG ATCTGGGTGA GTTGTGCGCA GCTCCCGGGA CACAAAACCC    660

AAACTCCCAA CCTCTGGATC AGGGAAGTTT CCTGGAAAGG TGAACCCCCG AGTTGAGCTG    720

AAGGACAAAT CACCTATGCC CATACGTGAG GGAAGGGGCC AGGCAGAAGA CGCAGCAGGA    780

GTGGGGACAC AGCAGGACCG AGGCCTGGCA TAACCCTGGC TGGCCTGCTG TGGCACAGAC    840

TGTGTCCATG GCCCCCTGTT CTGCCTCTCT CCCCACCATT AGACCACTGG AGAATACTCC    900

TTCAAGATCT TTCCAGAGAA AAACATTCGT GGCTTCAAGC TCCCAGACAC ACCTCAAGGC    960

CTCCTGGGGG AGGCCCGGAT GCTCAATGCC AGCATTGTGG CATCCTTCGT GGAGCTACCG   1020

CTGGCCAGCA TTGTCTCACT TCATGCCTCC AGCTGCGGTG AGCACCCTTC CCCTGCCCCT   1080

CCCTTCCCTT CCCTCCCTTG GATCAGTGGC CACACTGTTG GTGAAGCACC TCTGTGTGAG   1140

CTTGGGCAAG GTACATCAGC CTCTCTGAGC CTCATTTTTC TCATCTGCAC ATGGGAACAA   1200

TGGGAGTAGC TAATCATAGA AGAGCCTGAG AATCGCTTGA ACCTGGGAGA TGGAGGTTGC   1260

AGTGAGCCAA GATCGTGCCA CTGCACTCCC AGCCCGGGTA ACAGAGCAAA ACTCCGTCTC   1320

AAAAAAAAAA AAAAAAAAA AAAAGCCTGG TGCGGCACAC ATATCACACA GTGACCAGCC   1380

GCCTGGCCTG CCTCTNCNAC CCCACAGGTG                                   1410

(2) INFORMATION FOR SEQ ID NO:15:

(i) SEQUENCE CHARACTERISTICS:
        (A) LENGTH: 389 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:15:

TGGTAGGCTG CAGACCTCAC CCGCACCGAT CCAGACCACT CCTCCCAAGG ACACTTGTAG     60

CCCGGAGCTG CTCATGTCCT TGATCCAGAC AAAGTGTGCC GACGACGCCA TGACCCTGGT    120

ACTAAAGAAA GAGCTTGTTG CGTAAGGGAA CTCCTGCCCC TCTGGCTCAG GATGACATGG    180

ACATCTGGTT CCTCCCCTAG CCCAAGACTC TTGGGGTCCT AGCCCAGGCA GGGGGGCAAG    240

TCACGTCCCT CTGCAAGCCT TAGTTTTCCC ACTTGTATAA TGGAATTGAT AATGGTACCT    300

ACCACGTGGT GAGAATTAAA GGCAGTCTGA CAGGCCAATC ACGTGGCACA GTAAGATGTG    360

CTTAGTAAAT AATGCAGCAC TAGGTAGTT                                     389

(2) INFORMATION FOR SEQ ID NO:16:

(i) SEQUENCE CHARACTERISTICS:
        (A) LENGTH: 178
        (B) TYPE: nucleic acid
        (C) STRANDEDNESS: double
        (D) TOPOLOGY: linear (ii) MOLECULE TYPE: DNA (genomic)

(ix) SEQUENCE DESCRIPTION: SEQ ID NO: 16:
```

```
GCATTTGAAG TGCACCATCA CGGGCCTGAC CTTCTGGGAC CCCAGCTGTG AGGCAGAGGA      60

CAGGGGTGAC AAGTTTGTCT TGCGCAGTGC TTACTCCAGC TGTGGCATGC AGGTGTCAGC     120

AAGTATGATC AGCAATGAGG CGGTGGTCAA TATCCTGTCG AGCTCATCAC CACAGCGG      178
```

(2) INFORMATION FOR SEQ ID NO:17:

(i) SEQUENCE CHARACTERISTICS:
        (A) LENGTH: 311 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:17:

```
GATCGCACCA CTGCACTCCA GCCTGGGCGA CAGAGCGAGA CTCCGTCTCA AAAAAAAAAA      60

AAAGAGAGT CAGGCAACTC CACAGGGCCA TGATGCCTGT TCCTCCCCAC ACCCCTCGCC     120

CTCCTGGCTG GCGCCGCCAG ATTGACCAAG TCTCCCTCCC GTCCTCCCCA GAAAAGGTG     180

CACTGCCTCA ACATGGACAG CCTCTCTTTC CAGCTGGGCC TCTACCTCAG CCCACACTTC    240

CTCCAGGCCT CCAACACCAT CGAGCCGGGG CAGCAGAGCT TTGTGCAGGT ACCTGGCATG    300

CCTGTCACCC T                                                          311
```

(2) INFORMATION FOR SEQ ID NO:18:

(i) SEQUENCE CHARACTERISTICS:
        (A) LENGTH: 656 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:18:

```
TTCCTCTAAC CGACCTTTCT TCCCACCATG ACTCCAGAGG AGATGAGACT CCCAGAGTCA      60

GGAGGGAGAC AGCCTGGGTG CACAGGGAGA GGGAGAGACA GAGAAGGCAT TGCTCAGGGA    120

CACTGACAAG GATGTGGCCC TGTCCTCCTC CTCTGCCCCA GTACAGGTCC ATGTCTTTCT    180

TTCCACTGTG AGGACTCAGG GGTGGGAACT CTTAATTCTA GCCGATATTT GAAGGCAGCA    240

GGTGGGGTGG GGTGAAGAGC AGCTGCCCAT GCCGGTGGCC CTACCTACCC ATGCAGGTCA    300

GAGTGTCCCC ATCCGTCTCC GAGTTCCTGC TCCAGTTAGA CAGCTGCCAC CTGGACTTGG    360

GGCCTGAGGG AGGCACCGTG GAACTCATCC AGGGCCGGGC GGCCAAGGGC AACTGTGTGA    420

GCCTGCTGTC CCCAAGCCCC GAGGGTGACC CGCGCTTCAG CTTCCTCCTC CACTTCTACA    480

CAGTACCCAT ACCCAAAACC GGCACCCTCA GCTGCACGGT AGCCCTGCGT CCCAAGACCG    540

GGTCTCAAGA CCAGGTGAGT GGGGCCTGGG CGGCCAGCTT CAAGTGGGAG CTTCCAGGTC    600

TGTGGTTTGC ATGGAAGGGA CATGGCAGCC CACAGGATGT GGCCAGCTGG TGAGGG        656
```

(2) INFORMATION FOR SEQ ID NO:19:

(i) SEQUENCE CHARACTERISTICS:
        (A) LENGTH: 1576 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:19:

-continued

```
GATCTTCCAG GACTCACCCA GAGGCATCCA GCTACGAAGC GGTGGAGATG GGATTCAAAG      60

CCAAGGCTCT AGGGTGGGCT GGGGTCACGG AGCCAGGGAG TAAACCTGGA AGCCGCCTCC     120

CAAAGGTGCC ACATACTGCT CTCTCTTTCT CCTCCAGGAA GTCCATAGGA CTGTCTTCAT     180

GCGCTTGAAC ATCATCAGCC CTGACCTGTC TGGTGAGCTC CCTCCAGGTC TCTCGGGTTT     240

GTTCTAGTGG CTGAGGTCAC AGTAGGGCAC AGCGGGCAGC CCTGAGAACG GCCTGGCACA     300

TAGCACATGG CAAGGTGGAC CCTCTAGGTG GACAGTCCTA GCAACCATGG CTCAATCAGG     360

CCTGGCTGTG ATGAGCCCGT TTGCTGCAAG AGGAGACTGA GGTTCAGAGA AGTCGAGGGT     420

CCATGGCTCA GCAGAGCTGG CACCAAACCC ACATGGGCCA GCACAACAGG GTAGGGGATG     480

GGGCAGGGGC AGAGTGGCAG TGCTGATTGG CGTCGGCCTC TCTAGGTTGC ACAAGCAAAG     540

GCCTCGTCCT GCCCGCCGTG CTGGGCATCA CCTTTGGTGC CTTCCTCATC GGGGCCCTGC     600

TCACTGCTGC ACTCTGGTAC ATCTACTCGC ACACGCGTGA GTACCCCAGG CCCCCACAGT     660

GAGCATGCCG GGCCCCTCCA TCCACCCGGG GGAGCCCAGT GAAGCCTCTG AGGGATTGAG     720

GGGCCCTGGC AGGACCCTGA CCTCCGCCCC TGCCCCCGCT CCCGCTCCCA GGTTCCCCCA     780

GCAAGCGGGA GCCCGTGGTG GCGGTGGCTG CCCCGGCCTC CTCGGAGAGC AGCAGCACCA     840

ACCACAGCAT CGGGAGCACC CAGAGCACCC CCTGCTCCAC CAGCAGCATG GCATAGCCCC     900

GGCCCCCCGC GCTCGCCCAG CAGGAGAGAC TGAGCAGCCG CCAGCTGGGA GCACTGGTGT     960

GAACTCACCC TGGGAGCCAG TCCTCCACTC GACCCAGAAT GGAGCCTGCT CTCCGCGCCT    1020

ACCCTTCCCG CCTCCCTCTC AGAGGCCTGC TGCCAGTGCA GCCACTGGCT TGGAACACCT    1080

TGGGGTCCCT CCACCCCACA GAACCTTCAA CCCAGTGGGT CTGGGATATG GCTGCCCAGG    1140

AGACAGACCA CTTGCCACGC TGTTGTAAAA ACCCAAGTCC CTGTCATTTG AACCTGGATC    1200

CAGCACTGGT GAACTGAGCT GGGCAGGAAG GGAGAACTTG AAACAGATTC AGGCCAGCCC    1260

AGCCAGGCCA ACAGCACCTC CCCGCTGGGA AGAGAAGAGG GCCCAGCCCA GAGCCACCTG    1320

GATCTATCCC TGCGGCCTCC ACACCTGAAC TTGCCTAACT AACTGGCAGG GGAGACAGGA    1380

GCCTAGCGGA GCCCAGCCTG GGAGCCCAGA GGGTGGCAAG AACAGTGGGC GTTGGGAGCC    1440

TAGCTCCTGC CACATGGAGC CCCCTCTGCC GGTCGGGCAG CCAGCAGAGG GGGAGTAGCC    1500

AAGCTGCTTG TCCTGGGCCT GCCCCTGTGT ATTCACCACC AATAAATCAG ACCATGAAAC    1560

CTGAAAAAAA AAAAAA                                                    1576
```

(2) INFORMATION FOR SEQ ID NO:20:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

```
CCTCATAAGG TGGCTGTGAT GATG                                             24
```

(2) INFORMATION FOR SEQ ID NO:21:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

CATCTGCCTT GGAGCTTCCT CT                    22

(2) INFORMATION FOR SEQ ID NO:22:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

TTCCTGACCT CCTACATGG                        19

(2) INFORMATION FOR SEQ ID NO:23:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:23:

CTCTTGGTGC CCAAGTTT                         18

(2) INFORMATION FOR SEQ ID NO:24:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:24:

CGGGCTCTGT TAGGTGCAG                        19

(2) INFORMATION FOR SEQ ID NO:25:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:25:

GGGTGGGGCT TTATAAGGGA                       20

(2) INFORMATION FOR SEQ ID NO:26:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:26:

CTGTCCGCTT CAGTGTTCCA TC                    22

(2) INFORMATION FOR SEQ ID NO:27:

(i) SEQUENCE CHARACTERISTICS:
       (A) LENGTH: 24 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:27:

GGAAACTTCC CTGATCCAGA GGTT                                          24

(2) INFORMATION FOR SEQ ID NO:28:

(i) SEQUENCE CHARACTERISTICS:
       (A) LENGTH: 18 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:28:

GAGGCCTGGC ATAACCCT                                                 18

(2) INFORMATION FOR SEQ ID NO:29:

(i) SEQUENCE CHARACTERISTICS:
       (A) LENGTH: 18 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:29:

GTGGCCACTG ATCCAAGG                                                 18

(2) INFORMATION FOR SEQ ID NO:30:

(i) SEQUENCE CHARACTERISTICS:
       (A) LENGTH: 23 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:30:

ACACATATCA CACAGTGACC AGC                                           23

(2) INFORMATION FOR SEQ ID NO:31:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:31:

CTAGGGGAGG AACCAGATGT C                                             21

(2) INFORMATION FOR SEQ ID NO:32:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:32:

AGATTGACCA AGTCTCCCTC CC                                                    22

(2) INFORMATION FOR SEQ ID NO:33:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:33:

AGGCTGTCTC CCTCCTGACT CT                                                    22

(2) INFORMATION FOR SEQ ID NO:34:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:34:

ACTCAGGGGT GGGAACTCTT                                                       20

(2) INFORMATION FOR SEQ ID NO:35:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:35:

CCTTCCATGC AAACCACAG                                                        19

(2) INFORMATION FOR SEQ ID NO:36:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:36:

GAGTAAACCT GGAAGCCGC                                                        19

(2) INFORMATION FOR SEQ ID NO:37:

(i) SEQUENCE CHARACTERISTICS:
            (A) LENGTH: 20 base pairs
            (B) TYPE: nucleic acid
            (C) STRANDEDNESS: single -continued (D) TOPOLOGY: linear (ii) MOLECULE TYPE: DNA (genomic)

(xi) SEQUENCE DESCRIPTION: SEQ ID NO:37:

GCCACTAGAA CAAACCCGAG                                                    20

(2) INFORMATION FOR SEQ ID NO:38:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:38:

CCAGCACAAC AGGGTAGGGG AT                                                 22

(2) INFORMATION FOR SEQ ID NO:39:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:39:

CTCAGAGGCT TCACTGGGCT CC                                                 22

(2) INFORMATION FOR SEQ ID NO:40:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:40:

TGAAGCCTCT GAGGGATTGA GG                                                 22

(2) INFORMATION FOR SEQ ID NO:41:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:41:

GAGTTCACAC CAGTGCTCCC AG                                                 22